(12) United States Patent
Cui et al.

(10) Patent No.: US 8,314,933 B2
(45) Date of Patent: Nov. 20, 2012

(54) OPTOFLUIDIC MICROSCOPE DEVICE WITH PHOTOSENSOR ARRAY

(75) Inventors: Xiquan Cui, Pasadena, CA (US); Xin Heng, Emeryville, CA (US); Lap Man Lee, Pasadena, CA (US); Changhuei Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 601 days.

(21) Appl. No.: 12/398,050

(22) Filed: Mar. 4, 2009

(65) Prior Publication Data

US 2011/0181884 A1 Jul. 28, 2011

Related U.S. Application Data

(60) Provisional application No. 61/068,131, filed on Mar. 4, 2008.

(51) Int. Cl.
*G01N 21/00* (2006.01)
(52) U.S. Cl. .......................................... 356/436; 356/440
(58) Field of Classification Search .......... 356/432–436, 356/338; 382/152
See application file for complete search history.

(56) References Cited

U.S. PATENT DOCUMENTS

| | | | |
|---|---|---|---|
| 4,438,330 A | 3/1984 | Hardy | |
| 4,692,027 A | 9/1987 | MacGovern et al. | |
| 4,737,621 A | 4/1988 | Gonsiorowski et al. | |
| 4,981,362 A | 1/1991 | DeJong et al. | |
| 5,196,350 A | 3/1993 | Backman et al. | |
| 5,362,653 A | 11/1994 | Carr et al. | |
| 5,426,505 A | 6/1995 | Geiser et al. | |
| 5,795,755 A | 8/1998 | Lemelson | |
| 5,798,262 A | 8/1998 | Garini et al. | |
| 5,973,316 A | 10/1999 | Ebbesen et al. | |
| 6,143,247 A | 11/2000 | Sheppard, Jr. et al. | |

(Continued)

FOREIGN PATENT DOCUMENTS

EP    1371965    12/2003

(Continued)

OTHER PUBLICATIONS

Adams, Mark L. et al., "Microfluidic Integration on detector arrays for absorption and flourescence micro-spectrometers," 2003, Sensors and Actuators A, vol. 104, pp. 25-31.

(Continued)

*Primary Examiner* — Layla Lauchman
(74) *Attorney, Agent, or Firm* — Weaver Austin Villeneuve & Sampson LLP; Sheila Martinez-Lemke

(57) ABSTRACT

Embodiments of the present invention relate to techniques for improving optofluidic microscope (OFM) devices. One technique which may be used eliminates the aperture layer covering the light detector layer. Other techniques retain the aperture layer, reversing the relative position of the light source and light detector such that light passes through the aperture layer before passing through the fluid channel to the light detector. Another technique adds an optical tweezer for controlling the movement of objects moving through the fluid channel. Another technique adds an optical fiber bundle to relay light from light transmissive regions to a remote light detector. Another technique adds two electrodes at ends of the fluid channel to generate an electrical field capable of moving objects through the fluid channel while suppressing rotation. These techniques can be employed separately or in combination to improve the capabilities of OFM devices.

9 Claims, 17 Drawing Sheets

U.S. PATENT DOCUMENTS

| | | | |
|---|---|---|---|
| 6,499,499 | B2 | 12/2002 | Dantsker et al. |
| 6,753,131 | B1 | 6/2004 | Rogers et al. |
| 6,858,436 | B2 | 2/2005 | Zenhausern et al. |
| 7,045,781 | B2 | 5/2006 | Adamec et al. |
| 7,250,598 | B2 | 7/2007 | Hollingsworth et al. |
| 7,271,885 | B2 | 9/2007 | Schermer |
| 7,283,229 | B2 | 10/2007 | Noguchi et al. |
| 7,641,856 | B2 * | 1/2010 | Padmanabhan et al. ......... 422/73 |
| 7,671,987 | B2 * | 3/2010 | Padmanabhan et al. ....... 356/338 |
| 7,738,695 | B2 | 6/2010 | Shorte et al. |
| 7,751,048 | B2 | 7/2010 | Yang et al. |
| 7,768,654 | B2 | 8/2010 | Cui et al. |
| 7,773,227 | B2 | 8/2010 | Yang et al. |
| 2003/0142291 | A1 | 7/2003 | Padmanabhan et al. |
| 2003/0174992 | A1 | 9/2003 | Levene et al. |
| 2003/0203502 | A1 | 10/2003 | Zenhausern et al. |
| 2004/0156610 | A1 | 8/2004 | Charlton et al. |
| 2004/0175734 | A1 | 9/2004 | Stahler et al. |
| 2004/0224380 | A1 | 11/2004 | Chou et al. |
| 2005/0271548 | A1 | 12/2005 | Yang et al. |
| 2006/0003145 | A1 | 1/2006 | Hansen et al. |
| 2006/0013031 | A1 | 1/2006 | Ravkin et al. |
| 2007/0207061 | A1 | 9/2007 | Yang et al. |
| 2007/0258096 | A1 | 11/2007 | Cui et al. |
| 2009/0225319 | A1 | 9/2009 | Lee et al. |
| 2009/0276188 | A1 | 11/2009 | Cui et al. |

FOREIGN PATENT DOCUMENTS

| | | |
|---|---|---|
| JP | 2003207454 | 7/2003 |
| JP | 2003524779 | 8/2003 |
| WO | WO0210713 | 2/2002 |
| WO | WO2004038484 | 5/2004 |

OTHER PUBLICATIONS

Beebe, David J. et al., "Physics and Applications of Microfluidics in Biology," 2002, Annu. Rev. Biomed., Eng., vol. 4, pp. 261-286.

Bethe, H.A., "Theory of Diffraction by Small Holes," 1944, The Physical Review, vol. 66, Nos. 7-8, pp. 163-182.

Biddiss, Elaine et al., "Hetergeneous Surface Charge Enhanced Micromixing for Electrokinetic Flows," 2004, Anal. Chem., vol. 76, pp. 3208-3213.

Boppart, S.A. et al., "Forward-imaging instruments for optical coherence tomography," 1997, Optics Letters, vol. 22, pp. 1618-1620.

Cao, Jinhua et al., "Brownian Particle Distribution in Tube Flows," 2004, Proceedings of IMECE04, vol. 260, pp. 243-252.

Cheng, Ya et al., "Microfluidic laser embedded in glass by three-dimensional femtosecond laser microprocessing," 2004, Optics Letters, vol. 29, No. 17, pp. 2007-2009.

Chronis, Nikolas et al., "Total internal reflection-based biochip utilizing a polymer-filled cavity with a micromirror sidewall," 2004, Lab Chip, vol. 4, pp. 125-130.

Courjon, Daniel, "Near-field Microscopy and near-field optics," 2003, Imperial College Press, 317 pages.

Dahan, M. et al., "Time-gated biological imaging by use of collidal quantum dots," 2001 Optics Letters, vol. 26, No. 11, pp. 825-827.

De Abajo, F.J. Garcia, "Light transmission through a single cylindrical hole in a metallic film," 2002, Optics Letters, vol. 10, No. 25, pp. 1475-1484.

De Fornel, F., "Evanascent waves from Newtonian optics and Atomic optics," 2001, Springer, 270 pages.

Heng, Xin et al., "Optofluidic Microscopy," 2005, Proceedings of the ICMM 2005 3rd International Conference on Microchannels and Minichannels, pp. 1-6.

Jaiswal, Jyoti K. et al., "Long-term multiple color imaging of live cells using quantum dot biconjugates," 2003, Nature Biotechnology, vol. 21, pp. 47-51.

Nott, Prabhu R. et al., "Pressure-driven flow of suspensions: simulation and theory," 1994, J. Fluid Mech., vol. 275, pp. 157-199.

Segre, G. et al., "Behavior of macroscopic rigid spheres in Poiseuille flow: Part 1. Determination of local concentration by statistical analysis of particle passages through crossed light beams," 1962, J. Fluid Mech., vol. 14, pp. 115-135.

Segre, G. et al., "Behavior of macroscopic rigid spheres in Poiseuille flow: Part 2. Experimental results and interpretation," 1962, J. Fluid Mech., vol. 14, pp. 136-157.

Seo, Jeonggi et al., "Disposable integrated microfluidics with self-aligned planar microlenses," 2004, Sensors and Acutators B, vol. 99, pp. 615-622.

Spring, Kenneth R. et al., "Introduction to Fluorescence Microscopy," Aug. 25, 2004, <http://www.microscopyu.com/articles/fluorescence/fluorescenceintro.html>.

Stone, H.A. et al., "Engineering Flows in Small Devices: Microfluidics Toward a Lab-on-a-Chip," 2004, Annu. Rev. Fluid Mech., vol. 36, pp. 381-411.

Tearney, G.J. et al., "Scanning single-mode fiber optic catheter-endoscope for optical coherence tomography," 1996, Optics Letters, vol. 21, pp. 543-545.

Thorsen, Todd et al., "Microfluidic Large-Scale Integration," 2002, Science, vol. 298, pp. 580-584.

Chovin, Arnaud, et al., "Fabrication, Characterization, and Far-Field Optical Properties of an Ordered Array of Nanoapertures," Nano Letters, vol. 4, No. 10, pp. 1965-1968 (2004).

Creath, K., "Phase-Measurement interferometry techniques," Prog. Opt., vol. 26, p. 44 (1988).

Cui, Xiquan, et al., "Lensless high-resolution on-chip optofluidic microscopes for *Caenorhabditis elegans* and cell imaging," Proceedings of the National Academy of Science, vol. 105, p. 10670 (2008).

Cui, Xiquan, et al., "Portable optical microscope-on-a-chip," Photonics West, San Jose, CA (Jan. 2006).

Cui, Xiquan, et al., "Quantitative differential interference contrast microscopy based on structured-aperture interference," Applied Physics Letters, vol. 93, pp. 091113-1-091113-3 (2008).

Cui, Xiquan, et al., "Slanted hole array beam profiler (SHArP)—a high-resolution portable beam profiler based on a linear aperture array," Optics Letters, vol. 31, No. 21, pp. 3161-3163 (2006).

Heng, Xin, et al., "Optofluidic Microscope, a miniature microscope on a chip," 9th International Converence on Miniaturized Systems for Chemistry and Life Sciences (μTAS) (2005).

Heng, Xin, et al., "Optofluidic Microscopy—a method for implementing a high resolution optical microscope on a chip," Lab Chip, vol. 6, pp. 1274-1276 (2006).

Heng, Xin, et al., "An Optical Tweezer Actuated, Nanoaperture-grid based Optofluidic Microscope Implementation Method," Optics Express, vol. 15, No. 25, 16367-16375 (2007).

Lay, Christophe, et al., "Enhanced microfiltration devices configured with hydrodynamic trapping and a rain drop bypass filtering architecture for microbial cells detection," Lab Chip 2008, 8:830-833; published as Advanced Article on Apr., 1, 2008 at http://pubs.rsc.org | DOI:10.1039/b800015h.

Lee, Lap Man, et al., "The Application of On-Chip Optofluidic Microscopy for Imaging *Giardia lamblia* Trophozoites and Cysts," Biomed Microdevices, Springer DOI 10.1007/s10544-009-9312-x (2009).

Lew, Matthew et al., "Interference of a four-hole aperture for on-chip quantitative two-dimensional differential phase imaging," Optic Letters, vol. 32, No. 20, pp. 2963-2965 (Oct. 2007).

Nozokido, Tatsuo, et al., "Scanning Near-Field Millimeter-Wave Microscopy Using a Metal Slit as a Scanning Probe," IEEE Transactions on Microwave Theory and Techniques, vol. 49, No. 3, 491-99 (2001).

Psaltis, Demetri, et al., "Developing optofluidic technology through the fusion of microfluidics and optics," Nature, vol. 442 (2006).

Probstein, R. F., "Physicochemical Hydrodynamics," Wiley, 2nd Edition pp. 109-116, 123, 190-197, and 309-310 (2003).

Walker, Glenn, and Beebe, David, "A Passive Pumping Method for Microfluidic Devices," Lab Chip, pp. 131-134 (2002).

Zhu, Liang, et al., "Filter-based microfluidic device as a platform for immunofluorescent assay of microbial cells," Lab Chip, 2004, vol. 4, pp. 337-341; published as Advanced Article on Apr. 5, 2004 at http://pubs.rsc.org | DOI: 10.1039/b401834f.

Albensi, B. C., et al., "Elements of Scientific Visualization in Basic Neuroscience Research," BioScience, vol. 54, pp. 1127-1137 (2004).

Arnison, M. R., et al., "Linear Phase Imaging Using Differential Interference Contrast Microscopy," Journal of Microscopy, vol. 214, Part. I, pp. 7-12 (Apr. 2004).

Betzig, E., et al.,"Imaging intracellular fluorescent proteins at nanometer resolution," Science, vol. 313, pp. 1642-1645 (2006).

Bouwkamp, C. J., "Diffraction theory," Reports on Progress in Physics XVIII, pp. 35-100 (1954).

Doyle, P. S., et al., "Self-assembled magnetic matrices for DNA separation chips," Science, vol. 295, No. 5563, p. 2237 (Mar. 2002).

Dunn, et al., "Introduction to Confocal Microscopy," available from MicroscopyU at http://www.microscopyu.com/articles/confocal (2007).

Ebbesen, T. W., et al., "Extraordinary optical transmission through sub-wavelength hole arrays," Nature, vol. 391, No. 6668, pp. 667-669 (Feb. 1998).

Fowles, Introduction to Modern Optics, Dover, Second Ed., p. 57-61. (1989).

Fu, A. Y., et al., "A microfabricated fluorescence-activated cell sorter," Nature Biotechnology, vol. 17, No. 11, pp. 1109-1111 (Nov. 1999).

Haglund, M. M., et al., "Enhanced optical imaging of human gliomas and tumor margins," Neurosurgery, vol. 38, pp. 308-317 (1996).

Heng, Xin, et al., "Characterization of light collection through a subwavelength aperture from a point source," Optics Express, vol. 14, pp. 10410-10425 (2006).

Hoffman, R., and Gross L., "The modulation contrast microscope," Nature, vol. 254, pp. 586-588 (1975).

Hogenboom, C. A., et al., "Three-dimensional images generated by quadrature interferometry," Optics Letters, vol. 23, pp. 783-785 (1998).

Lezec, H.J., et al. "Beaming Light from a Subwavelength Aperture," Science, vol. 297, No. 5582, pp. 820-822 (2002).

Lezec, H.J., and Thio, T., "Diffracted evanescent wave model for enhanced and suppressed optical transmission through subwavelength hole arrays," Optics Express, vol. 12, No. 16, pp. 3629-3651 (Aug. 2004).

Liang, J. Z., et al., "Supernormal vision and high-resolution retinal imaging through adaptive optics," Journal of the Optical Society of America, vol. 14, No. 11, pp. 2884-2892 (Nov. 1997).

Liu, S. R., "A microfabricated hybrid device for DNA sequencing," Electrophoresis 2003, vol. 24, No. 21, pp. 3755-3761 (2003).

Marquet, P. et al., "Digital holographic microscopy: a noninvasive contrast imaging technique allowing quantitative visualization of living cells with subwavelength axial accuracy," Optics Letters, vol. 30, No. 5, pp. 468-470 (Mar. 2005).

Murphy, et al., "Differential Interference Contrast (DIC)," available from Nikon MicrocopyU at http://www.microscopyu.com/articles/dic/dicindex.html (2007).

Popescu, G., et al., "Optical measurement of cell membrane tension," Physical Review Letters 97 (2006).

Rappaz, B., et al., "Measurement of the integral refractive index and dynamic cell morphometry of living cells with digital holographic microscopy," Optics Express, vol. 13, pp. 9361-9373 (2005).

Rust, M. J., et al., "Sub-diffraction-limit imaging by stochastic optical reconstruction microscopy (STORM)," Nature Methods, vol. 3, pp. 793-795 (2006).

Schwiegerling, J. and Neal, D. "Historical development of the Shack-Hartmann wavefront sensor," in Robert Shannon and Roland Shack: Legends in Applied Optics, edited by J. E. Harvey and R. B. Hooker_ SPIE, Bellingham, WA, pp. 132-139 (2005).

Sommer, R.J, and Sternberg, P.W., "Changes of induction and competence during the evolution of vulva development in nematodes," Science 265, pp. 114-118 (1994).

Stanley, S.L., "Amoebiasis," Lancet 361, pp. 1025-1034 (2003).

Tegenfeldt, J. O., et al., "Micro- and nanofluidics for DNA analysis," Analytical and Bioanalytical Chemistry, vol. 378, No. 7, pp. 1678-1692 (2004).

Tegenfeldt, J. O., et al., "Near-field Scanner for Moving Molecules," Physical review letters, vol. 86, No. 7, pp. 1378-1381 (Feb. 2001).

Thompson, R. E., et al., "Precise nanometer localization analysis for individual fluorescent probes," Biophysical Journal, vol. 82, No. 5, pp. 2775-2783 (May 2002).

Tokeshi, M. et al., "Chemical processing on microchips for analysis, synthesis, and bioassay," Electrophoresis, vol. 24, No. 21, pp. 3583-3594 (2003).

Trau, D. et al., "Genotyping on a complementary metal oxide semiconductor silicon polymerase chain reaction chip with integrated DNA microarray," Analytical Chemistry, vol. 74, No. 13, pp. 3168-3173 (2002).

International Search Report in International Application PCT/US2009/036045 (Apr. 23, 2009).

Written Opinion in International Application PCT/US2009/036045 (Apr. 23, 2009).

International Search Report in International Application PCT/US2009/036052 (Jun. 29, 2009).

Written Opinion in International Application PCT/US2009/036052 (Jun. 29, 2009).

International Search Report in International Application PCT/US2005/016876 (Oct. 16, 2006).

Written Opinion in International Application PCT/US2005/016876 (Oct. 16, 2006).

International Search Report in International Application PCT/US2008/054908 (Aug. 26, 2008).

Written Opinion in International Application PCT/US2008/054908 (Aug. 26, 2008).

European Patent Office (EPO) Office Action in EP Application No. 05749488.2 (Jan. 16, 2012).

European Patent Office (EPO) Office Action in EP Application No. 08730664.3 (Feb. 7, 2012).

Japanese Patent Office (JPO) Office Action in JPO patent Application No. 2007-515164 (Jul. 26, 2011).

Japanese Patent Office (JPO) Office Action in JPO patent Application No. 2007-515164 (May 8, 2012).

Japanese Patent Office (JPO) Office Action in JPO patent Application No. 2009-553675 (Jan. 24, 2012).

United States Patent and Trademark Office (USPTO) Office Action in U.S. Appl. No. 12/797,132 (Oct. 15, 2010).

United States Patent and Trademark Office (USPTO) Office Action in U.S. Appl. No. 12/785,635 (Oct. 15, 2010).

United States Patent and Trademark Office (USPTO) Office Action in U.S. Appl. No. 11/743,581 (May 22, 2009).

United States Patent and Trademark Office (USPTO) Office Action in U.S. Appl. No. 11/743,581 (Dec. 3, 2009).

United States Patent and Trademark Office (USPTO) Notice of Allowance in U.S. Appl. No. 11/743,581 (Mar. 26, 2010).

United States Patent and Trademark Office (USPTO) Office Action in U.S. Appl. No. 11/686,095 (Jan. 10, 2008).

United States Patent and Trademark Office (USPTO) Office Action in U.S. Appl. No. 11/686,095 (Jul. 17, 2008).

United States Patent and Trademark Office (USPTO) Office Action in U.S. Appl. No. 11/686,095 (Feb. 26, 2009).

United States Patent and Trademark Office (USPTO) Office Action in U.S. Appl. No. 11/686,095 (Oct. 28, 2009).

United States Patent and Trademark Office (USPTO) Notice of Allowance in U.S. Appl. No. 11/686,095 (Feb. 25, 2010).

United States Patent and Trademark Office (USPTO) Office Action in U.S. Appl. No. 11/125,718 (Jul. 1, 2009).

United States Patent and Trademark Office (USPTO) Office Action in U.S. Appl. No. 11/125,718 (Nov. 14, 2008).

United States Patent and Trademark Office (USPTO) Office Action in U.S. Appl. No. 12/398,098 (May 23, 2011).

United States Patent and Trademark Office (USPTO) Notice of Allowance in U.S. Appl. No. 12/792,059 (Mar. 14, 2012).

United States Patent and Trademark Office (USPTO) Office Action in U.S. Appl. No. 13/157,245 (Dec. 6, 2011).

United States Patent and Trademark Office (USPTO) Office Action in U.S. Appl. No. 12/398,050 (Nov. 14, 2011).

United States Patent and Trademark Office (USPTO) Office Action in U.S. Appl. No. 12/398,098 (May 25, 2011).

United States Patent and Trademark Office (USPTO) Notice of Allowance in U.S. Appl. No. 12/638,518 (Apr. 23, 2012).

United States Patent and Trademark Office (USPTO) Notice of Allowance in U.S. Appl. No. 12/638,518 (Feb. 14, 2012).

* cited by examiner

OPTOFLUIDIC MICROSCOPE DEVICE WITH PHOTOSENSOR ARRAY

STATEMENT AS TO RIGHTS TO INVENTIONS MADE UNDER FEDERALLY SPONSORED RESEARCH OR DEVELOPMENT

The U.S. Government has certain rights in this invention pursuant to Grant No. EB005666 awarded by the National Institutes of Health and Grant No. HR0011-04-1-0032 awarded by DARPA.

CROSS-REFERENCES TO RELATED APPLICATIONS

This is a non-provisional patent application that claims the benefit of the filing date of U.S. Provisional Patent Application No. 61/068,131 entitled "Optofluidic Microscope" filed on Mar. 4, 2008. That provisional application is hereby incorporated by reference in its entirety for all purposes.

This non-provisional application is related to the following co-pending and commonly-assigned patent applications, which are hereby incorporated by reference in their entirety for all purposes:

U.S. patent application Ser. No. 11/125,718 entitled "Optofluidic Microscope Device" filed on May 9, 2005, now U.S. Pat. No. 7,773,227.

U.S. patent application Ser. No. 11/686,095 entitled "Optofluidic Microscope Device" filed on Mar. 14, 2007, now U.S. Pat. No. 7,751,048.

U.S. patent application Ser. No. 11/743,581 entitled "On-chip Microscope/Beam Profiler based on Differential Interference Contrast and/or Surface Plasmon Assisted Interference" filed on May 2, 2007, now U.S. Pat. No. 7,768,654.

The following non-provisional patent application is being filed on the same day and is hereby incorporated by reference in its entirety for all purposes: U.S. patent application Ser. No. 12/398,098, entitled "Methods of Using Optofluidic Microscope Devices".

BACKGROUND OF THE INVENTION

Embodiments of the present invention generally relate to optofluidic microscope devices. More specifically, certain embodiments relate to techniques for improving optofluidic microscope (OFM) devices.

Microscopes and other optical microscopy devices are used extensively in all aspects of modern biomedicine and bioscience. Typically, conventional microscopes include an objective lens, a platform for supporting an object, and an eyepiece containing lenses for focusing images. These conventional microscope designs have bulky optics, and have proven to be expensive and difficult to miniaturize.

Some advances in optical microscopy promise to provide more compact systems but have presented significant technical barriers. For example, near field scanning optical microscopes (NSOMs) use a strongly enhanced and tightly confined optical field (near field) at the end of an NSOM probe tip to optically probe a specific location on an object. NSOMs can optically resolve structures with spatial resolutions of ~50 nm. In addition, NSOM imaging methods are non-destructive and can be used to image objects that are immersed in buffer media. NSOMs are however restricted to detecting light in the near field. Moreover, NSOMs have difficulty performing imaging at high throughput rates (i.e., high numbers of objects being imaged per unit time).

Some microscopy systems have eliminated lenses altogether. FIG. 1(a) is a schematic drawing of a top view of a lensless microscopy system. In this system, an object 10 being imaged is placed directly onto a light detector 11 (e.g., a complementary-symmetry metal-oxide-semiconductor (CMOS) light detector) having a two dimensional array of light detecting elements. The light detector 11 takes a snapshot image 32 of the object 10. The resolution of the snapshot image 102 is generally limited by the size of each light detecting element (e.g., pixel size).

FIG. 1(b) is a schematic drawing of a top view of another lensless microscopy system. The light detector 11 in this system is covered by an aperture layer 14 (e.g., a thin metal layer) with small apertures (holes). The apertures are formed in the aperture layer 14 at locations corresponding to the center of each discrete light detecting element in the light detector. Each light detecting element is generally only sensitive to light transmitted through the aperture above it. Since the apertures are small and relatively widely spaced at a pixel width apart, the light being transmitted through the apertures is a sparse sampling of the light being transmitted through to the aperture layer 14. By placing an object 10 above the aperture layer 14, a sparsely sampled image 34 of the object 10 can be generated. The sparsely sample image 34 may have a better resolution than images generated by the system shown in FIG. 1(a). The resolution of the image is however limited by the pixel size of the light detecting elements of the light detector 11.

FIG. 1(c) is a schematic drawing of a top view of the system of FIG. 1(b) where raster-scanning is employed to take time varying data to generate a filled-in image 36. The filled-in image 36 can be generated by raster-scanning the object 10 over the aperture layer 14 (or raster-scanning the aperture layer 14 over the object 10) and compositing the time varying transmissions of light through the apertures detected by the light detecting elements through the apertures. Since time varying data is used, the resolution of the filled-in image 36 is improved in the x-direction. However, the resolution is limited in the y-direction by the size of each light detecting element (e.g., pixel size).

BRIEF SUMMARY OF THE INVENTION

Embodiments of the present invention relate to techniques improving OFM devices. One technique which may be used eliminates the aperture layer covering the light detector layer. Other techniques retain the aperture layer, reversing the relative position of the light source and light detector such that light passes through the aperture layer before passing through the fluid channel to the light detector. Another technique adds an optical fiber bundle to relay light from light transmissive regions (such as apertures) to a remote light detector. This technique allows the light detector to be isolated from the light transmissive regions.

Additional techniques can be used to control the fluid flow and/or objects through the fluid channel. One technique that can be used adds one or more electrodes outside a surface of the fluid channel to attract objects to the surface. Another technique adds two electrodes at ends of the fluid channel to generate an electrical field capable of moving objects through the fluid channel while suppressing rotation. Another technique adds an injection unit for introducing objects into the fluid channel and two focusing units that use fluid flow to appropriately position objects in the fluid channel. Another technique adds a laser (optical tweezer) for controlling the movement of objects moving through the fluid channel.

Other techniques add filters and/or use fluorescence to improve the capabilities of OFM devices. The above techniques, together with others specifically mentioned below, can be employed separately or in combination to improve the capabilities of OFM devices.

One embodiment is directed to an OFM device comprising a body defining a fluid channel having a longitudinal axis. The body includes a surface layer proximal to the fluid channel. The OFM device also comprises a one-dimensional array of light detecting elements located within the surface layer. The light detecting elements are configured to receive light passing through the fluid channel and generate time-varying data associated with the received light as an object passes through the fluid channel. The one-dimensional array of light detecting elements extends substantially from a first lateral side to a second lateral side of the fluid channel.

Another embodiment is directed to a method comprising causing an object to move through a fluid channel and providing light to the fluid channel using an illumination source while the object is moving through the fluid channel. The method also comprises receiving light from the illumination source passing through the fluid channel with an array of light detecting elements located in a surface layer of a body of the OFM device. The surface layer is proximal to the fluid channel. The one-dimensional array of light detecting elements extends substantially from a first lateral side to a second lateral side of the fluid channel. The method also comprises generating data associated with the received light by the array of light detecting elements, generating line scans using a processor based on the data generated by the array of light detecting elements, and assembling the line scans using the processor to generate an image of the object.

One embodiment is directed to an OFM device comprising a body defining a fluid channel and having light transmissive regions. The OFM devices also comprises a first one-dimensional array of light detecting elements configured to receive light from an illumination source through the light transmissive regions and generate data associated with the received light and a second one-dimensional array of light detecting elements substantially parallel to the first one-dimensional array of light detecting elements. The light detecting elements in the second one-dimensional array are configured to receive light through the light transmissive regions and generate additional data associated with the light.

One embodiment is directed to an OFM device comprising a body defining a fluid channel. The body includes an aperture surface layer proximal to the fluid channel and on a first side of the fluid channel, and an additional layer on a second side of the fluid channel opposing the first side. The OFM device also comprises an illumination source configured to provide illumination into the fluid channel through light transmissive regions in the aperture surface layer and a one-dimensional array of light detecting elements located in the additional layer. The light detecting elements are configured to receive light from the fluid channel and generate time varying data associated with the received light.

One embodiment is directed to an OFM device comprising a body defining a fluid channel, light transmissive regions in the body, a light detector, and an optical fiber bundle. The optical fiber bundle has a first end in optical communication with the fluid channel and configured to receive light from an illumination source through the light transmissive regions, and a second end in optical communication with the light detector.

One embodiment is directed to an OFM device comprising a body defining a fluid channel. The body includes a surface layer proximal to the fluid channel. The OFM device also comprises an array of light detecting elements in the body configured to receive light from the fluid channel and generate data associated with the received light, and an electrode located in the body outside the surface layer. The electrode is configured to generate a positive charge for attracting an object moving through the fluid channel to the surface layer.

One embodiment is directed to an OFM device comprising a body defining a fluid channel having a longitudinal axis and an array of light detecting elements in the body. The array of light detecting element is configured to receive light from an illumination source through the fluid channel and generate data associated with the received light. The OFM device also comprises a first electrode and a second electrode at different locations along the longitudinal axis of the fluid channel. The first electrode and the second electrode are configured to generate an electrical field that moves an object through the fluid channel in a direction parallel to the longitudinal axis of the fluid channel while substantially preventing rotation of the object.

One embodiment is directed to an OFM device comprising a body defining a fluid channel and an array of light detecting elements in the body. The array of light detecting elements is configured to receive light from the fluid channel and generate data associated with the received light. The OFM device also includes an injection unit configured to introduce an object into the fluid channel and a first focusing unit and a second focusing unit configured to generate fluid flow to move the object to a portion of the fluid channel.

One embodiment is directed to an OFM device comprising a body defining a fluid channel, an array of light detecting elements in the body, and configured to receive light from the fluid channel and generate data associated with the received light, and a laser for controlling movement of one or more objects moving through the fluid channel.

One embodiment is directed to an OFM device comprising a body defining a fluid channel. The body includes a surface layer proximal to the fluid channel. The OFM device also comprises light transmissive regions in the surface layer and a first filter located outside the surface layer, the first filter configured to pass light of a wavelength re-emitted from fluorophores in an object moving through the fluid channel. The OFM device also comprises a one-dimensional array of light detecting elements located outside the first filter, and configured to receive light passing through the first filter.

One embodiment is directed to an OFM device comprising a body defining a fluid channel. The body includes a surface layer proximal to the fluid channel. The OFM device also comprises a plurality of slits in the surface layer. The slits have different orientations with respect to a longitudinal axis of the fluid channel. The OFM device also comprises light detecting elements in the body, and configured to receive light through the slits and generate time varying data associated with the received light.

One embodiment is directed to an OFM device comprising an influx for receiving a sample, a body having a surface layer, and a plurality of OFM devices. Each OFM device comprises a fluid channel defined by the body, and adapted to receive a portion of the sample from the influx. The surface layer of the body is proximal to the fluid channel. The OFM device also comprises a one-dimensional array of light detecting elements located within the surface layer. The light detecting elements are configured to receive light passing through the fluid channel and generate time-varying data associated with the received light as the sample passes through the fluid channel. The one-dimensional array of light detecting elements extends substantially from a first lateral side to a second lateral side of the fluid channel.

These and other embodiments of the invention are described in further detail below.

DETAILED DESCRIPTION OF THE INVENTION

Embodiments of the present invention will be described below with reference to the accompanying drawings. One embodiment includes a technique for improving an OFM device by eliminating the aperture layer formerly located over the light detector layer. The OFM device of this embodiment has a body that defines a fluid channel having an upper surface and a lower surface. The body of the OFM device has a surface layer that coincides with the lower surface of the fluid channel. The illumination source is located above the upper surface of the fluid channel and provides light of suitable wavelengths onto an object (e.g., cell or micro-organism) travelling with a flow through the fluid channel.

An optical detector is in the surface layer of the body and receives light passing through the object from the illumination source and/or light re-emitted from fluorophores in the object. The optical detector includes individual light detecting elements (e.g., pixels) in the form of a one-dimensional array diagonally extending across the fluid channel. Since the one-dimensional array is diagonally positioned, the spacing between the light detecting elements across the fluid channel may be smaller than the size of the light detecting element (i.e., pixel size). With this diagonal arrangement, the resolution in the y-direction is independent of the pixel size and the optofluidic microscope is capable of imaging objects at much higher resolutions than a pixel size.

The light detecting elements in the one-dimensional array take time varying readings of the light that they receive as the object travels through the fluid channel. These time varying readings can be used to generate line scans. The time varying readings are also used to determine the rotation and velocity of the object. The OFM device uses the line scans while accounting for rotation and velocity of the object to construct an image of the object.

The OFM device of this embodiment has a simpler design than other OFM devices since it eliminates the aperture layer with light transmissive regions (apertures). This simpler design may be less expensive to manufacture. In addition, eliminating the aperture layer may improve the quality of the image generated by the OFM device as described below with respect to FIG. 2(a) and FIG. 2(b).

Figure 1A:
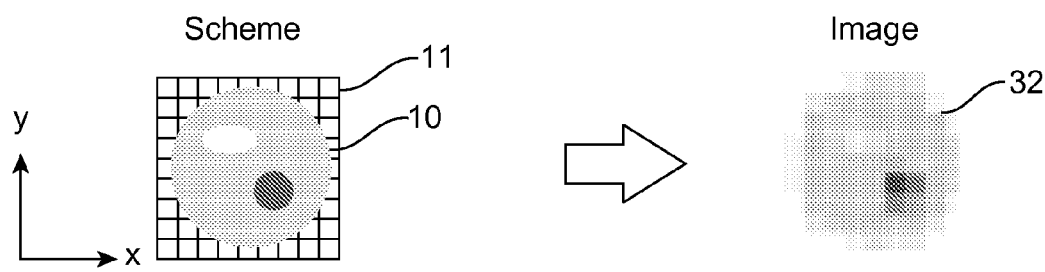
FIG. 1(a) is a schematic drawing of a top view of a lensless microscopy system.
Figure 1B:
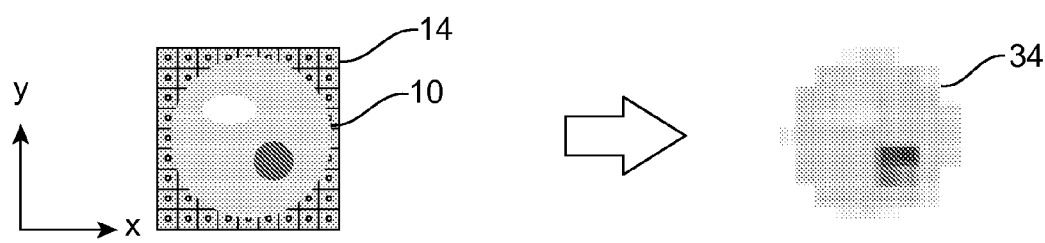
FIG. 1(b) is a schematic drawing of a top view of another lensless microscopy system.
Figure 1C:
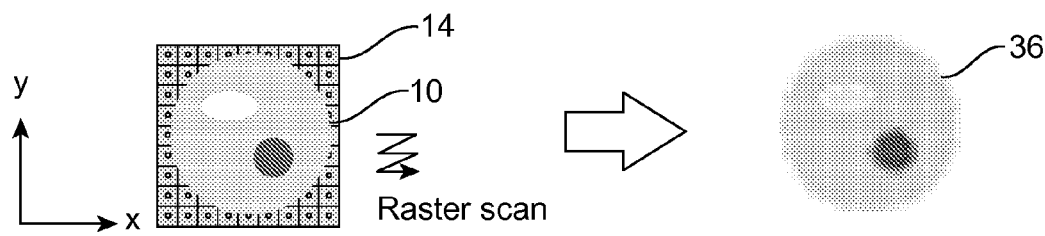
FIG. 1(c) is a schematic drawing of a top view of the system of FIG. 1(b) where raster-scanning is employed to take time varying data to generate a filled-in image.
Figure 2A:
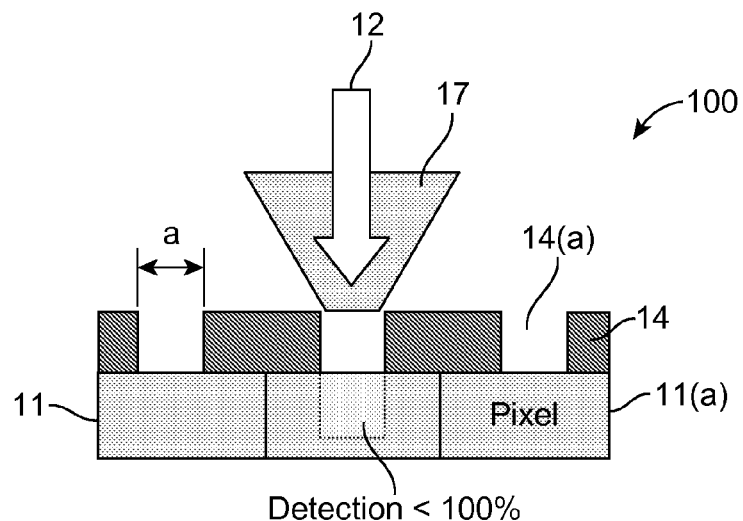
FIG. 2(a) is a cross-sectional view taken along a diagonal line showing components of an OFM device having an aperture layer, according to an embodiment of the invention.

FIG. 2(a) is a cross-sectional view taken along a diagonal line showing components of an OFM device 100 having an aperture layer 14, according to an embodiment of the invention. Three light transmissive regions 14(a) (e.g., holes) with a width "a" are shown. As illustrated, the light transmissive regions 14(a) can cause a scattering 17 of the light from an illumination source 12 at the entrance of the light transmissive regions 14(a). This scattering of light can reduce the intensity of the light received by the light detector 11 on the other side of the light transmissive regions 14(a). Due to the scattering, the light intensity detected by the light detector 11 is less than 100% of the illumination intensity originating from the illumination source 12. The detection by the light detector 11 is represented by the shaded region in the pixel. The image quality can be affected more by stray light (noise) when the detected light intensity is relatively low.

Figure 2B:
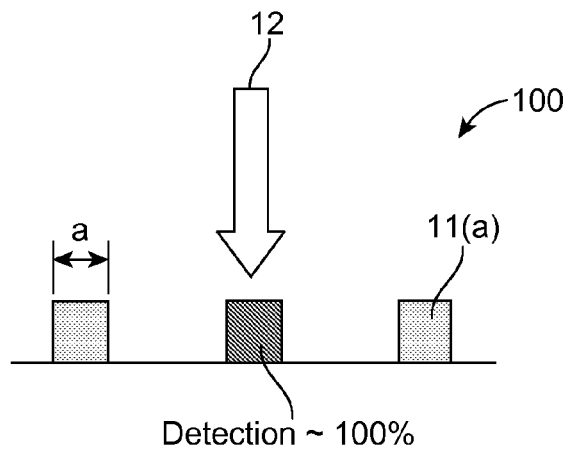
FIG. 2(b) is a schematic drawing of a side view of components of an OFM device that does not include an aperture layer, according to an embodiment of the invention.

Eliminating the aperture layer 14 avoids the scattering of light due to the light transmissive regions which may improve the signal-to-noise ratio and the image quality. FIG. 2(b) is a schematic drawing showing a cross-sectional view along a diagonal of components of an OFM device 10 that does not include an aperture layer 14, according to an embodiment of the invention. In this illustrated example, the light from the illumination source 12 is substantially unobstructed before reaching the light detecting element 11(a) (pixel). In this case, the light intensity detected is approximately 100% of the illumination intensity from the illumination source 12. This detection is represented by the light detecting element 11(a) being completely shaded. The OFM device in this example eliminates the aperture layer 14, and can provide images with a better signal-to-noise ratio than OFM devices having an aperture layer 14 under the same illumination intensity.

In general, OFM devices of embodiments of the invention provide advantages because, relative to conventional microscopes, they are inexpensive, compact, and lensless. Tens or even hundreds of individual OFM devices can be placed on a single compact device. The ability to use a multitude of microscopes on a single compact device allows for parallel imaging of large populations of cells or microorganisms. Parallel imaging allows for high throughput rates. This makes OFM devices of embodiments of the invention highly suited for various clinical applications. Moreover, OFM devices may be inexpensive and disposable. In the clinical setting, the ability to dispose of the OFM devices could reduce potential cross-contamination risks between specimens. Further, embodiments of the invention can be designed for particular applications such as diagnosing illnesses like malaria. In a Third World environment, low-cost and compact microscope systems suitable for malaria diagnosis could be a boon for health workers who often have limited access to medical facilities and need to travel from village to village.

I. OFM (Optofluidic Microscope) Device Configurations

Three configurations of OFM devices 100 are described below. The first configuration includes an OFM device 100 having an aperture layer 14 covering the light detecting elements 11(a) in the light detector 11 and the illumination source above the object 10. The second configuration eliminates the aperture layer 14. A third configuration locates the illumination source under the fluid channel and locates the light detector 11 over the fluid channel.

A. First Configuration

Figure 3A:
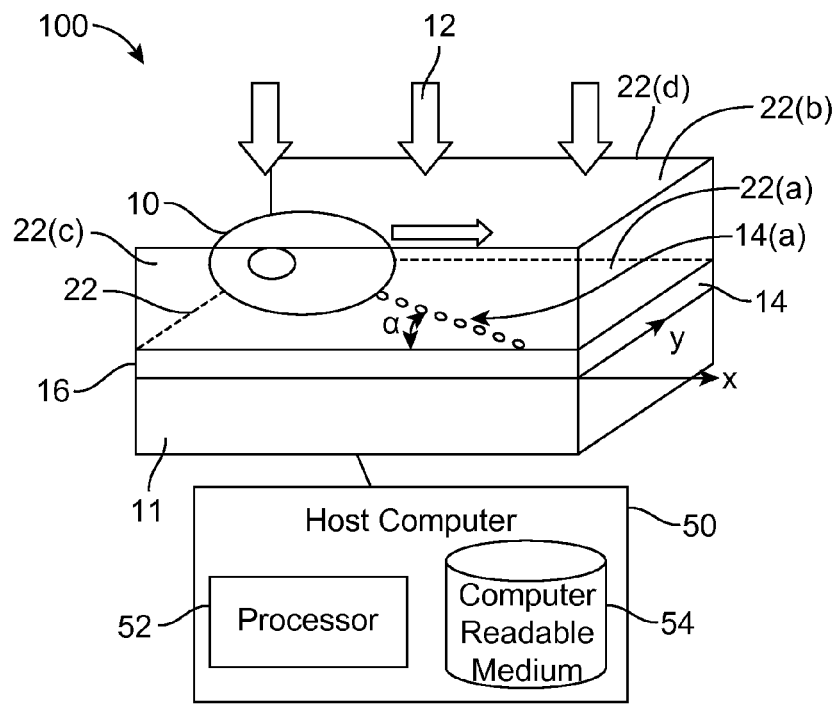
FIG. 3(a) is a schematic drawing of a perspective view of components of an OFM device in a first configuration, according to embodiments of the invention.

FIG. 3(a) is a schematic drawing of a perspective view of components of an OFM device 100 in a first configuration, according to embodiments of the invention.

The OFM device 100 includes a body 16 which defines or includes a fluid channel 22. The fluid channel 22 includes a first surface 22(a) and a second surface 22(b) on opposite sides of the fluid channel 22. The first surface 22(a) may correspond to an inner surface at the bottom of the fluid channel 22 and the second surface 22(b) may correspond to the inner surface at the top of the fluid channel 22. The fluid channel 22 also includes two opposing lateral surfaces 22(c) and 22(d).

The body 16 can be a multi-layer structure or a single, monolithic structure. In the illustrated example, the body 16 is a multi-layer structure having an opaque or semi-opaque aperture layer 14 that is an inner surface layer of fluid channel 22 having the first surface 22(a). The opaque or semi-opaque aperture layer 14 has light transmissive regions 14(a) in it. The opaque or semi-opaque aperture layer 14 can be a thin metallic layer in some cases. The body 16 may optionally include a transparent protective layer (not shown) that covers the opaque or semi-opaque aperture layer 14 to isolate the opaque or semi-opaque aperture layer 14 from the fluid and the object 10 moving through the fluid channel 22 of the OFM device 100.

The fluid channel 22 may have any suitable dimensions. For example, the width and/or height of the fluid channel 22 may each be less than about 10, 5, or 1 micron. In some embodiments, the fluid channel 22 may be sized based on the size of the objects 10 being imaged by the OFM device 100. For example, the height of the fluid channel 22 may be 10 micron where the objects 10 being imaged are 8 micron in order to keep the objects 10 close to the opaque or semi-opaque aperture layer 14, which may help improve the quality of the image. In most embodiments, the flow of the fluid in the fluid channel 22 is generally in the direction of the x-axis.

The OFM device 100 also includes a light detector 11 to the outside of the opaque or semi-opaque aperture layer 14. An illumination source 12 provides light through the second surface 22(b) of the fluid channel 22. As a fluid flows through the fluid channel 22, an object 10 in the fluid passes under the illumination source 12. The object 10 alters (e.g., blocks, reduces intensity, and/or modifies wavelength) the light through it to the light transmissive regions 14(a). The light detecting elements 11(a) detect light transmitted through the light transmissive regions 14(a).

The OFM device 100 also includes an x-axis and a y-axis that lie in the plane of the inner surface of the light detector 11 proximal to the fluid channel 22. The x-axis lies along a longitudinal axis of the fluid channel 22. The y-axis is orthogonal to the x-axis in the plane of the inner surface of the light detector 11.

The light transmissive regions 14(a) in the opaque or semi-opaque aperture layer 14 can be of any suitable shape and any suitable dimension. In the illustrated example, the light transmissive regions 14(a) are holes. The holes may be etched, for example, into the opaque or semi-opaque aperture layer 14 (e.g., a thin metallic layer). In another embodiment, the light transmissive regions 14(a) may be in the form of one or more slits. A slit can refer to an elongated opening such as a narrow rectangle. Each slit may have any suitable dimension. The slits may have uniform dimensions or may have variable dimensions. The slits can be oriented at any suitable angle or angles with respect to the x-axis of the fluid channel 22.

Figure 4:
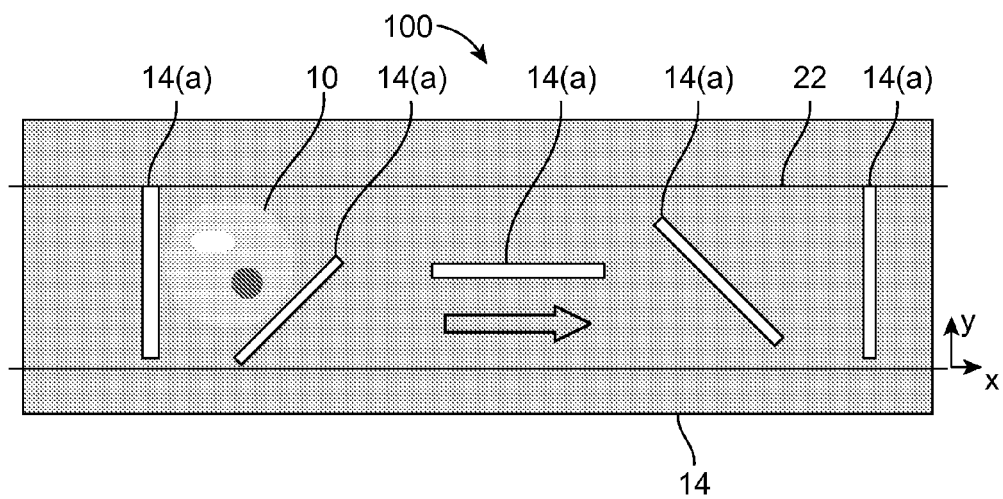
FIG. 4 is schematic drawing of components of an OFM device including light transmissive regions in the form of slits, according to an embodiment of the invention.

FIG. 4 is schematic drawing of a top view of components of an OFM device 100 including light transmissive regions 14(a) in the form of slits, according to an embodiment of the invention. The slits are arranged along the fluid channel 22 at multiple orientations. In other examples, the slits may be arranged in a single orientation or may extend across the fluid channel 22. One advantage to having slits is that slits may be less expensive to manufacture than holes. Another advantage is that the intensity of the light though a slit is greater than through a set of holes. If the light transmissions are higher, the signal to noise ratio may be higher which can improve the performance of the OFM device 100. An example of an aperture layer having a slit can be found in Nozokido, Tatsuo, Mizuno, Koji, *Scanning Near-Field Millimeter-Wave Microscopy Using a Metal Slit as a Scanning Probe*, IEEE Transactions on Microwave Theory and Techniques, Vol. 49, No. 3, (March 2001), which is hereby incorporated by reference in its entirety for all purposes.

The light transmissive regions 14(a) can be arranged in any suitable form. Some examples of suitable forms include a one-dimensional array, a two-dimensional array, and a multiplicity of one-dimensional and/or two-dimensional arrays. The arrays can have any suitable orientation or combination of orientations.

In FIG. 3(a), the light transmissive regions 14(a) are in the form of a single one-dimensional array which extends diagonally from one lateral surface 22(c) of the fluid channel 22 to the other lateral surface 22(d) of the fluid channel 22. The one-dimensional array is located at an angle, α with respect to the x-axis. The α can be any suitable angle.

Figure 5:
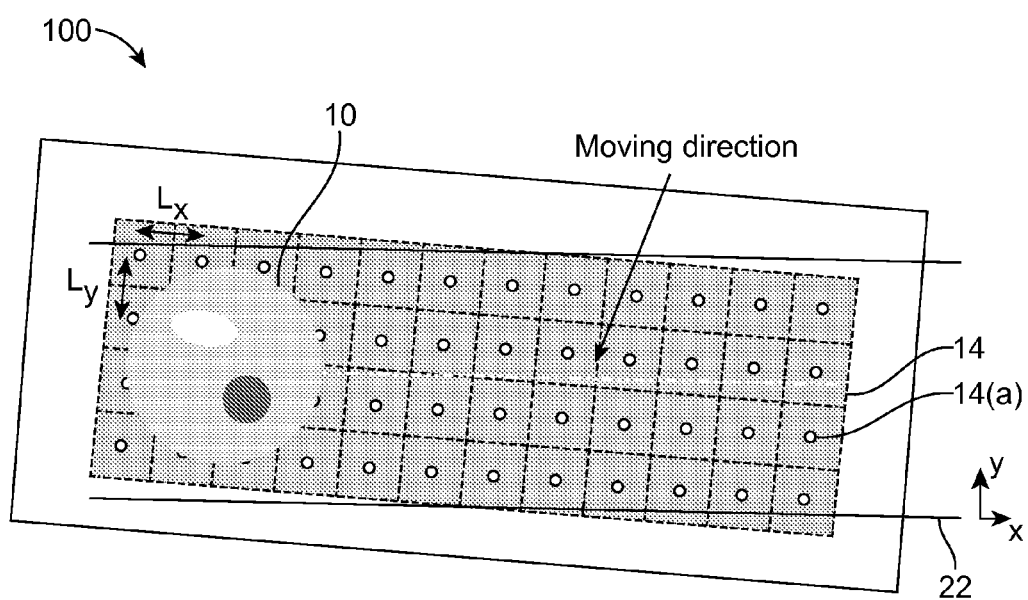
FIG. 5 is a schematic drawing of a top view of components of an OFM device having light transmissive regions in the form of a two-dimensional array oriented at an angle, a from the x-axis, according to an embodiment of the invention.

An example of a two-dimensional array can be found in FIG. 5, which is a schematic drawing of a top view of components of an OFM device 100 having light transmissive regions 14(a) in the form of a two-dimensional array oriented at an angle, α from the x-axis, according to an embodiment of the invention. In this example, the two-dimensional array replaces the lengthy one dimensional array. The two-dimensional array can represent four sections of the lengthy one-dimensional array shown in FIG. 3. By reducing the length of the array, the acquisition time for reading the information by the light detecting elements 11(a) may be reduced, which can increase throughput rates. Reducing acquisition time may also reduce the exposure of the object 10 to the illumination source 12, which can reduce the risk of burning the object 10. Reducing the acquisition time can also reduce the vulnerability of the object 10 to rotation and changing shape during acquisition. By avoiding these changes, the image quality can be improved and processing may be reduced. Further, reducing the length of the array can allow for a more compact OFM device 100.

The light detector 11 (e.g., photosensor) refers to any suitable device capable of detecting light and generating signals with data about the intensity, wavelength, and/or other information about the light being detected. The signals may be in the form of electrical current that results from the photoelectric effect. Some examples of suitable light detectors 11 include a charge coupled device (CCD) or a linear or two-dimensional array of photodiodes (e.g., avalanche photodiodes (APDs)) corresponding with the light transmissive regions 14(a). Light detector 11 could also be a complementary metal-oxide-semiconductor (CMOS) or photomultiplier tubes (PMTs). Other suitable light detectors 11 are commercially available.

The light detecting elements 11(a) of light detector 11 can be of any suitable size (e.g., 1-4 microns) and any suitable shape (e.g., circular or square). The light detecting elements 11(a) can be arranged in any suitable form such as a one-dimensional array, a two-dimensional array, and a multiplicity of one-dimensional and/or two-dimensional arrays. In some cases, the light detecting elements 11(a) can be arranged in the same form as the light transmissive regions 14(a). The arrays can have any suitable orientation or combination of orientations. In the illustrated example of FIG. 3, the light detecting elements 11(a) are in the faun of a one-dimensional array that corresponds to the one-dimensional array of light transmissive regions 14(a).

The illumination source 12 may be a component of the OFM device 100 or may separate from the OFM device 100. The illumination source 12 may be provided by any suitable device or other source of light such as ambient light. Any suitable wavelength and intensity of light may be used. For example, the illumination source 12 may provide light with a wavelength that will cause activation of fluorophores in the object 10. The illumination source 12 may be placed in any suitable location to provide light which can pass through the object 10 and the light transmissive regions 14(a) passing through the fluid channel 22. The light provided by the illumination source 12 may be modulated over time. Suitable illumination sources are naturally and commercially available.

The OFM device 100 also includes a host computer 50 communicatively coupled to the light detector 11. The host computer 50 comprises a processor 52 (e.g., a microprocessor) coupled to a computer readable medium 54 (CRM). Alternatively, the host computer 50 can be a separate device.

The processor 50 receives signals with time varying data from the light detecting elements 11(a) of the light detector 11 associated with the light received by the light detecting elements 11(a). The data may include the intensity of the light, the wavelength(s) of the light, and/or other information about the light received by the light detecting elements 11(a). The processor 50 executes code stored on the CRM 54 to perforin some of the functions of the OFM device 100 such as interpreting the time varying data from the light detector 11, generating line scans from the time varying data, and constructing an image of an object 10 moving through the fluid channel 22 from the line scans.

The CRM (e.g., memory) stores the code for performing some functions of the OFM device 100. The code is executable by the processor. In one embodiment, the CRM comprises a) code for distinguishing between different biological entities, b) code for determining the rotation and velocity of the object 10 using the data, c) code for determining changes in the shape of the object 10 using the data received from the light detecting elements 11(a), d) code for interpreting the time varying data received from the light detecting elements 11(a), e) code for performing suitable applications such as cross-correlation and fluorescence applications, f) code for generating line scans from the time varying data received from the light detecting elements 11(a), g) code for constructing one or more images from the line scans and/or other data such as rotation or changes in shape of the object 10, h) code for displaying the image, and i) any other suitable code for image processing. The CRM may also include code for performing any of the signal processing or other software-related functions that may be created by those of ordinary skill in the art. The code may be in any suitable programming language including C, C++, Pascal, etc.

Although not shown, the OFM device 100 may also include a display communicatively coupled to the processor. Any suitable display may be used. In one embodiment, the display may be a part of the OFM device 100. The display may provide information such as the image of the object 10 to a user of the OFM device 100.

Although the object 10 is shown as a cell in many embodiments, any suitable object 14 can be imaged by the OFM device 100. Suitable objects 10 can be biological or inorganic entities. Examples of biological entities include whole cells, cell components, microorganisms such as bacteria or viruses, cell components such as proteins, etc. Inorganic entities may also be imaged by embodiments of the invention.

During operation, a fluid, within which the object 10 is suspended, flows through the fluid channel 22. Any suitable mode (or modes) of controlling the flow of fluid and/or the movement of the object 10 can be employed. Any suitable devices such as micropumps, DC electrokinetic devices, dielectrophoresis electrodes, and/or hydrodynamic focusing channels can be used to control the flow of fluid and/or the movement of the object 10 through the fluid channel 22. Various modes of control are described in detail in Section V.

As the fluid flows through the fluid channel 22, the object 10 passes over the light transmissive regions 14(a). Light from the illumination source 12 passes through the fluid channel 22 and is altered (e.g., blocked, reduced intensity, and/or modified wavelength) by the object 10. The altered light passes through the light transmissive regions 14(a). Light that does not interact with the object 10 passes through the surface 22(a) of the fluid channel 22 to the light transmissive regions 14(a) and remains substantially unaltered with the exception of scattering.

As the object 10 passes through the fluid channel 22, the light detecting elements in the light detector 11 take data (e.g., intensity and wavelength readings) of light over time. This time varying data can be used to image the object 10. In the illustrated embodiment, each light transmissive region 14(a) and the transmission of light through the light transmissive region 14(a) uniquely maps to a single light detecting element 11(a). Each discrete light detecting element 11(a) in the light detector 11 generates time varying data that can be used to generate a line scan associated with locations along the y-axis. The time varying data is communicated in the form of a signal. The time varying data from the light detecting element 11(a) is dependent on the object profile as well as its optical properties. For example, time varying data that corresponds to low intensity of light at a predetermined position for a predetermined period of time may provide data regarding the length of the object at a particular position along the y-axis in the fluid channel 22. The time varying data from the light detecting elements can be processed using a processor to construct an image of the object 10 using line scans and, optionally, other data. In one example, it is presumed that the object 10 moves in a straight line as it passes through the fluid channel 22 and over the light detecting elements 11(a) in the light detector 11 and over the light transmissive regions 14(a). In other examples, certain data can be used to determine a rotation and velocity of the object 10 as it flows along the fluid channel 22. The time varying data for each light detecting element can then be processed using a processor to form an image of the object 10 that accounts for the rotation and/or the velocity of the object 10.

In some embodiments, the processor generates an image of the object 10 accounting for the velocity of the object 10 in the direction of the longitudinal axis of the fluid channel 22. The velocity in directions orthogonal to the longitudinal axis of the fluid channel 20 are assumed to be zero in many embodiments.

For the illustrated embodiment shown in FIG. 3(a), the achievable resolution in the direction of the y-axis (i.e. y direction) of the fluid channel 22, $r_y$, is based on the spacing of adjacent light transmissive regions 14(a) in this y direction. The more light transmissive regions 14(a) in the aperture layer 14 per unit width, the higher the achievable image resolution as defined by Eq. (1) below, $$r_y = \frac{w}{n_h}, \quad (1)$$

where $n_h$ equals to the number of light transmissive regions 14(a) and w is the channel width. For example, if the channel width is 40 μm, the y-direction image resolution would be 1 micron if there are 40 equally spaced light transmissive regions 14(a) extending across the entire width of the fluid channel 22. That is, the spacing between the adjacent light transmissive regions 14(a) in the direction of the y-axis approximates the achievable image resolution in the y direction.

In the direction of the x-axis of the fluid channel 22 (i.e. the x direction), the achievable image resolution is determined by the acquisition rate of data by the light detector 11 and the net velocity of the object 10 (i.e., the resolution in x-direction is equal to object moving speed, u, times the pixel acquisition time Δt) as defined by Eq. (2), $$r_x = u\Delta t, \quad (2)$$

For example, if the target flow speed is 100 microns per second, and the light detector's reading rate is 1 KHz, the maximum image resolution in the x direction would be equal to about 0.1 micron.

Figure 3B:
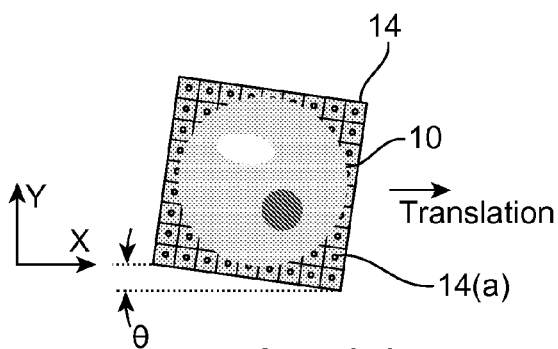
FIG. 3(b) is a schematic drawing of a top view of components of an OFM device, according to an embodiment of the invention.

FIG. 3(b) is a schematic drawing of a top view of components of an OFM device 100, according to an embodiment of the invention. The OFM device 100 includes an aperture layer 14 that covers the light detector 11 (shown in FIG. 3(a)). The aperture layer 14 has a two-dimensional array of light transmissive regions 14(a) oriented at an angle θ with respect to the longitudinal axis of the fluid channel 22. In the illustrated example, the light transmissive regions 14(a) are formed in the aperture layer 14 such that the two-dimensional array is aligned with the longitudinal axis of the aperture layer 14. The aperture layer 14 is rotated by the angle θ and then placed over the light detector 11. In other embodiments, the light transmissive regions 14(a) may be formed in the aperture layer 14 at an angle θ with respect to the longitudinal axis of the aperture layer 14.

Figure 3C:
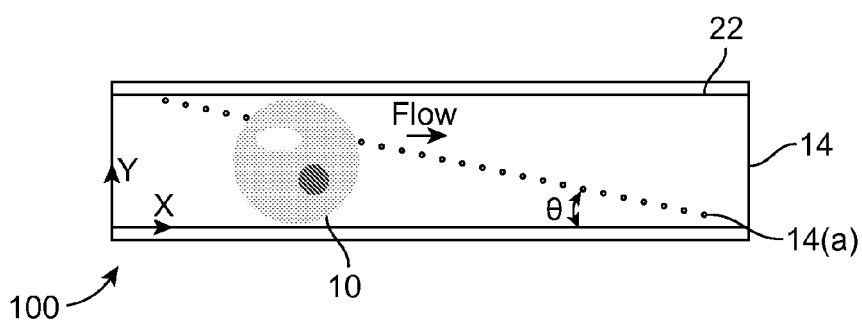
FIG. 3(c) is a schematic drawing of a top view of components of an OFM device, according to an embodiment of the invention.

FIG. 3(c) is a schematic drawing of a top view of components of an OFM device 100, according to an embodiment of the invention. The OFM device 100 includes an aperture layer 14 over the light detector 11 (shown in FIG. 3(a)). The aperture layer 14 includes light transmissive regions 14(a) in the form of a one-dimensional array (line) that is oriented at an angle (θ) from the x-axis. The OFM device 100 also includes a fluid channel 22 having a fluid within which the object 10 is suspended. The light transmissive regions 14(a) extend across the fluid channel 22. The light detecting elements 11(a) in the light detector 11 take time varying transmission data of light passing through the object 11 (or generated by fluorophores in the object) as the object 11 travels with the fluid flowing through the fluid channel 12. An image 40 can be generated by the optofluidic microscope device 100 using the time varying data generated by the light detecting elements 11(a).

B. Second Configuration

Figure 6:
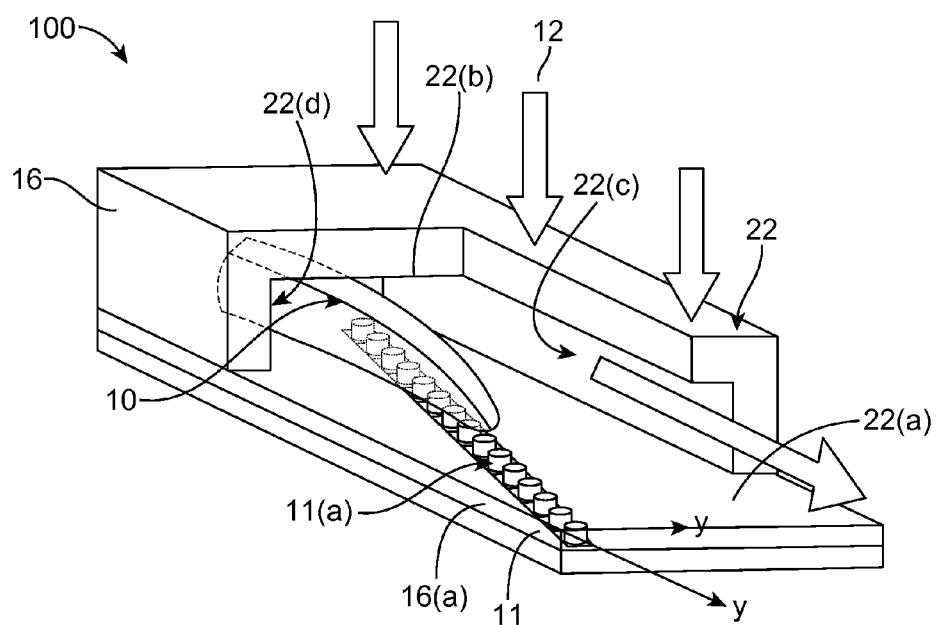
FIG. 6 is a schematic drawing of a perspective view of components of an OFM device in a second configuration, according to embodiments of the invention.

FIG. 6 is a schematic drawing of a perspective view of components of an OFM device 100 in a second configuration, according to an embodiment of the invention.

The OFM device 100 includes a body 16 which defines or includes a fluid channel 22, and a light detector 11 comprises light detecting elements 11(a). The fluid channel 22 includes a first surface 22(a) and a second surface 22(b) on opposite sides of the fluid channel 22. The first surface 22(a) may correspond to an inner surface at the bottom of the fluid channel 22 and the second surface 22(b) may correspond to the inner surface at the top of the fluid channel 22. The fluid channel 22 also includes two opposing lateral surfaces 22(c) and 22(d). The body 16 can be a multi-layer structure or a single, monolithic structure. In the illustrated example, the body 16 is a multi-layer structure having a surface layer 16(a) having the first surface 22(a) of the fluid channel 22. The light detecting elements 11(a) of the light detector 11 are located on or within the surface layer 16(a) of the body 16. In some cases, the surface layer 16(a) may be made of an opaque or semi-opaque layer that incorporates the light detecting elements 11(a). The fluid channel 22 may have any suitable dimensions.

The illumination source 12 provides light to the fluid channel 22 from outside the first surface 22(a) of the fluid channel 22. In other embodiments, the illumination source 12 may provide light from inside the fluid channel 22. As a fluid flows through the fluid channel 22, the object 10 passes over the light detecting elements 11(a) which can alter (e.g., block, reduce intensity, and/or modify wavelength) the light in some way. The light detecting elements 11(a) detect light that is not blocked.

The illumination source 12 may be a component of the OFM device 100 or may separate from the OFM device 100. Any suitable wavelength of light, intensity of light, or modulation parameters may be used.

The light detector 11 includes any suitable number and size of light detecting elements 11(a). In one embodiment, the light detecting elements 11(a) are less than or equal to one micron in diameter. Light detecting elements 11(a) can be any suitable shape such as circular, square, etc.

The light detecting elements 11(a) can be arranged in any suitable form such as a one-dimensional array, two-dimensional array, two or more one-dimensional arrays, a combination of different types of arrays, or other suitable form. If in the form of multiple arrays, the arrays can have any suitable orientation or combination of orientations.

Figure 11A:
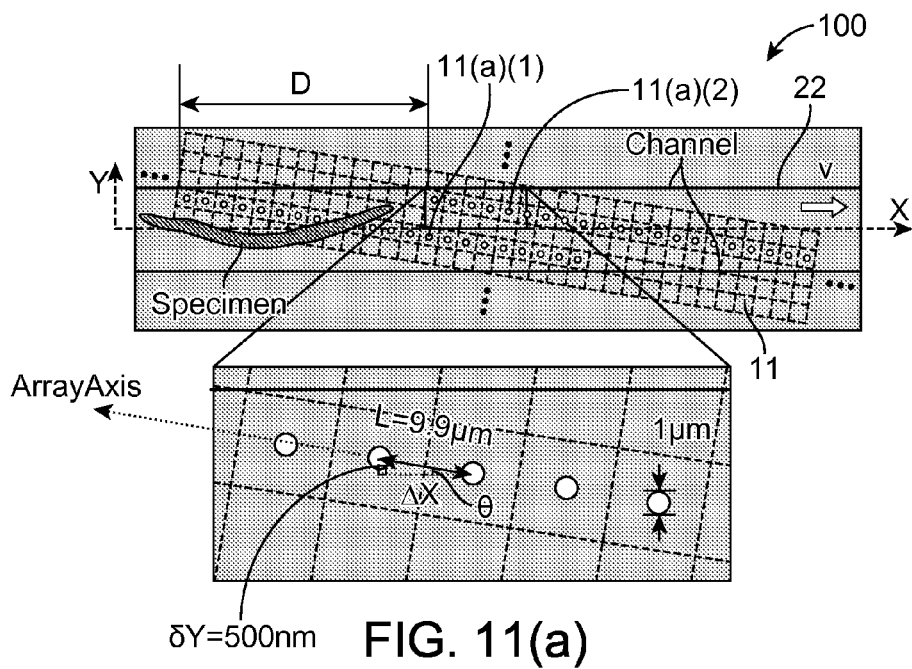
FIG. 11(a) is a schematic drawing of a top view of components of an OFM device, according to an embodiment of the invention.

In the illustrated example shown in FIG. 6, the light detector 11 includes a one-dimensional array of light detecting elements 11(a). In other embodiments, the light detecting elements 11(a) may be in the form of a two-dimensional array of light detecting elements 11(a) or multiple arrays (one-dimensional and/or two-dimensional) of light detecting elements 11(a). An example of light detecting elements 11(a) in the form of two one-dimensional arrays is shown in FIG. 11(a). The data taken from the light detecting elements 11(a) in multiple arrays can be used to measure the velocity of the object 10, the flow velocity, the rotation of the object 10, shape changes of the object 10. The data can also be used to cross correlate data derived from the light detecting elements 11(a) in the different arrays.

During operation, a fluid, within which the object 10 is suspended, flows through the fluid channel 22. Any suitable mode (or modes) of controlling the flow of fluid and/or the movement of the object 10 can be employed.

As the fluid flows through the fluid channel 22, the object 10 passes over the light detecting elements 11(a) of the light detector 11. Light from the illumination source 12 passes through the fluid channel 22 and is altered (e.g., blocked, reduced intensity, and/or modified wavelength) by the object 10. The altered light (e.g., reduced intensity, altered wavelength, etc.) passes to the light detecting elements 11(a). Light that does not interact with the object 10 passes to the light transmissive regions 14(a) as well.

Figure 7:
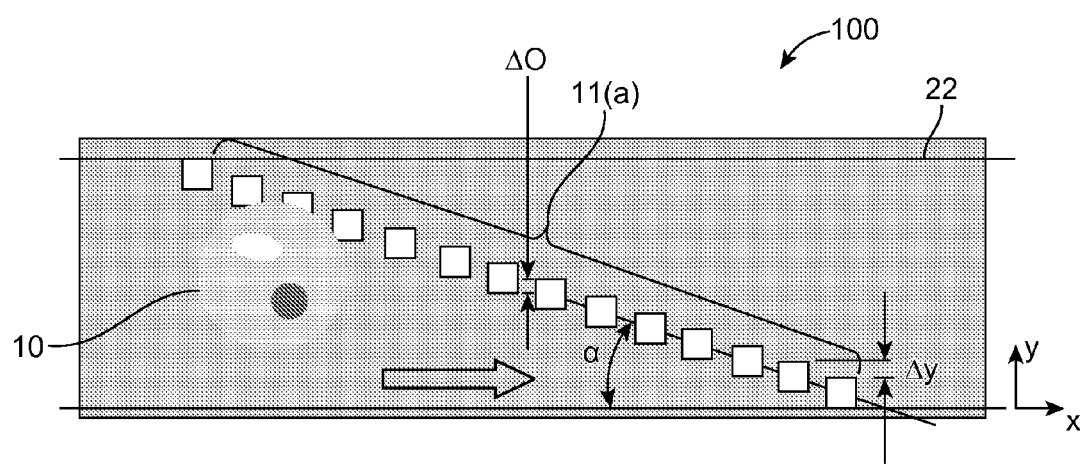
FIG. 7 is a schematic drawing of the top view of the fluid channel in the OFM device shown in FIG. 6, according to an embodiment of the invention.

FIG. 7 is a schematic drawing of the top view of components of the OFM device 100 of FIG. 6, according to an embodiment of the invention. As shown, the one-dimensional array of light detecting elements 11(a) extends from one lateral side of the fluid channel 22 to the other lateral side of the fluid channel 22. The one-dimensional array is oriented at an angle α with respect to the x-axis. The y-directional spacing between the light detecting elements 11(a), Δy 60 depends on the angle α.

In the illustrated embodiment, adjacent light detecting elements 11(a) have an overlap, Δo 60. Adjacent light detecting elements 11(a) in the array will provide time varying data associated with the same y locations within the overlap, ΔO 60. There will be overlapping coverage by the adjacent light detecting elements 11(a) at the y locations in overlap, ΔO 60. This overlapping time varying data from adjacent light detecting elements 11(a) at the overlap, ΔO 60 can be used to improve the quality of the image of the object 10 generated by the OFM device 100.

As the object 10 passes through the fluid channel 22, the light detecting elements transmit time varying data about the light received. The time varying data is processed using a processor to generate line scans associated with y-locations of the light detecting elements. The time varying data from the light detecting element 11(a) is dependent on the profile of the object 10 as well as its optical properties. The processor constructs an image of the object 10 using the line scans and optionally other data such as rotation, velocity of the object, changes in shape of the object, etc.

For the illustrated embodiment shown in FIG. 5 and FIG. 6, the achievable resolution in the direction of the y-axis (i.e. y direction) of the fluid channel 22, $r_y$, is based on the spacing of the adjacent light detecting elements 11(a) in the y direction. The more light detecting elements 11(a) per unit width, the higher the achievable image resolution as defined by Eq. (3) below, $$r_y = \frac{w}{n_h}, \tag{3}$$

where $n_h$ equals to the number of light detecting elements 11(a) and w is the channel width. For example, if the channel width is 40 μm, the y-direction image resolution would be 1 micron if there are 40 equally spaced light detecting elements 11(a) extending across the entire width of the fluid channel 22. That is, the spacing between the adjacent light detecting elements 11(a) in the direction of the y-axis approximates the achievable image resolution in the y direction.

In the direction of the x-axis of the fluid channel 22 (i.e. the x direction), the achievable image resolution is determined by the acquisition rate of data by the light detector 11 and the net velocity of the object 10 (i.e., the resolution in x-direction is equal to object moving speed, u, times the pixel acquisition time Δt) as defined by Eq. (4), $$r_x = u\Delta t, \tag{4}$$

For example, if the target flow speed is 100 microns per second and the light detector's reading rate is 1 KHz, the maximum image resolution in the x direction would be equal to about 0.1 micron.

The second configuration of components of the OFM device 100 may provide technical advantages. By eliminating the aperture layer 14 (shown in FIG. 3), the OFM device 100 is simplified and less expensive to manufacture. In addition, eliminating the aperture layer may improve the quality of the image generated by the OFM device. An aperture layer may cause scattering of the light which reduces the intensity of the light received the light detecting elements 11(a). The image quality is affected more by noise (stray) light when the detected light intensity is relatively low. Eliminating the aperture layer 14 reduces the risk of the scattering of light which may improve the signal-to-noise ratio and the image quality.

C. Third Configuration

Figure 8:
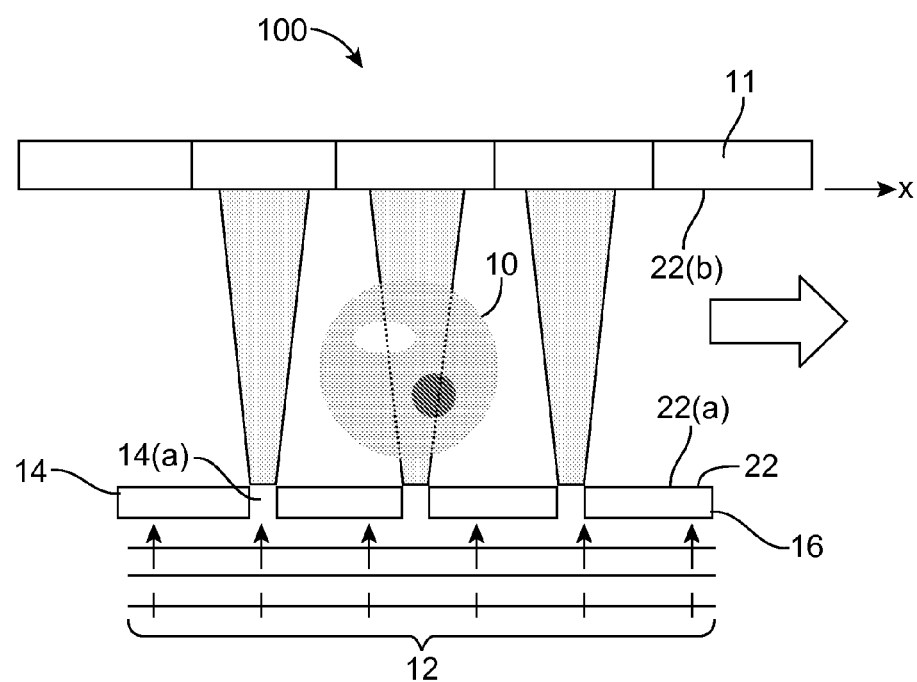
FIG. 8 is a schematic drawing of a side view of components of an OFM device in a third configuration, according to embodiments of the invention.

FIG. 8 is a schematic drawing of a side view of components of an OFM device 100 in the third configuration, according to embodiments of the invention.

The OFM device 100 includes a body 16 which defines or includes a fluid channel 22. The fluid channel 22 includes a first surface 22(a) and a second surface 22(b) on opposite sides of the fluid channel 22. The first surface 22(a) may correspond to an inner surface at the bottom of the fluid channel 22 and the second surface 22(b) may correspond to the inner surface at the top of the fluid channel 22. The fluid channel 22 also includes two opposing lateral surfaces 22(c) and 22(d). The body 16 may be made of any suitable material(s) and the fluid channel 22 may have any suitable dimensions.

The body 16 can be a multi-layer structure or a single, monolithic structure. In the illustrated example, the body 16 is a multi-layer structure having an opaque or semi-opaque aperture layer 14. The opaque or semi-opaque aperture layer 14 that is an inner surface layer of fluid channel 22 having the first surface 22(a). The opaque or semi-opaque aperture layer 14 has light transmissive regions 14(a) in it. The opaque or semi-opaque aperture layer 14 can be a thin metallic layer in some cases. The body 16 may optionally include a transparent protective layer (not shown) that covers the opaque or semi-opaque aperture layer 14 to isolate the opaque or semi-opaque aperture layer 14 from the fluid and the object 10 moving through the fluid channel 22 of the OFM device 100.

The opaque or semi-opaque aperture layer 14 has light transmissive regions 14(a) in it. The light transmissive regions 14(a) are of any suitable shape and any suitable dimension. In the illustrated example, the light transmissive regions 14(a) are apertures (holes). The holes may be etched in a thin metallic layer. In other embodiments, the light transmissive regions 14(a) may be in the faun of one or more slits. The light transmissive regions 14(a) can be arranged in any suitable form. Some examples of suitable forms include a one-dimensional array, a two-dimensional array, a series of one-dimensional arrays, or any suitable combination thereof. The arrays can have any suitable orientation or combination of orientations. In one exemplary embodiment, the light transmissive regions 14(a) are in the form of a one-dimensional array diagonally extending across the fluid channel 22 at an angle with respect to the x-axis or perpendicular to the x-axis.

The light detector 11 (e.g., photosensor) refers to any suitable device capable of detecting light and generating signals with data about the intensity, wavelength, and/or other information about the light being detected. The signals may be in the form of electrical current that results from the photoelectric effect. The light detector 11 includes any number or arrangement of light detecting elements 11(a). In one case, each light detecting element 11(a) may correspond to a single light transmissive region 14(a). Each light detecting element 11(a) can be of any suitable size and any suitable shape.

The illumination source 12 is located to the outside of the opaque or semi-opaque aperture layer 14 with respect to the fluid channel 22. The illumination source 12 may be located at any suitable distance from the outer surface of the opaque or semi-opaque aperture layer 14. The illumination source 12 produces light which passes through the light transmissive regions 14(a). As the light passes through the light transmissive regions 14(a), the light is converted into point illumination sources from the light transmissive regions 14(a). Light from the point illumination sources spreads out generally in a cone distribution from the light transmissive regions 14(a) into the fluid channel 22.

As the fluid flows through the fluid channel 22, the object 10 passes over the point illumination sources from the light transmissive regions 14(a). Light from the point illumination sources pass through the fluid channel 22 and is altered (e.g., blocked, reduced intensity, and/or modified wavelength) by the object 10. The altered light passes to the light detecting elements 11(a). Also, light that does not interact with the object 10 passes through to the light detecting elements 11(a).

As the object 10 passes through the fluid channel 22, the light detecting elements 11(a) transmit time varying data about the light received. The time varying data is processed to generate line scans associated with y-locations of the light detecting elements. The time varying data from the light detecting element 11(a) is dependent on the object profile as well as its optical properties. The processor constructs an image of the object 10 using the line scans and optionally other data such as rotation, velocity of the object, changes in shape of the object, etc.

The third configuration may provide technical advantages. In this configuration, the object 10 is sparsely illuminated by the point illumination sources as the object 10 moves through the fluid channel 22. Since the object is sparsely illuminated, it is subjected to less light during image acquisition which reduces the risk of damaging (e.g., burning) to the object 10. In addition, the light detecting elements 11(a) in this configuration can be relatively large to collect the light from the cone shaped distribution from the light transmissive regions 14(a) on the other side of the fluid channel 22. Larger light detecting elements 11(a) generally have higher light detection efficiency which improves performance.

II. Other Components of OFM Devices

A. Image Processing Components

The OFM devices 100 of embodiments of the invention may include image processing components. The image processing components may include a processor (e.g., a microprocessor) coupled to a computer readable medium (CRM), and other suitable devices. Alternatively or additionally, the OFM device 100 may be communicatively coupled to a computer having a processor coupled to a CRM. The computer may process data communicated from the OFM device 100.

The processor may be integrated or separate from the light detector 11. The processor receives signals with time varying data from the light detecting elements 11(a) of the light detector 11 associated with the light received by the light detecting elements 11(a). The data may include the intensity of the light, the wavelength(s) of the light, and/or other information about the light received by the light detecting elements 11(a). The processor executes code for performing some of the functions of the OFM devices 100.

The CRM (e.g., memory) stores the code for performing the functions of the OFM device 100. The code is executable by the processor. In one embodiment, the CRM comprises a) code for distinguishing between different biological entities, b) code for determining the rotation and velocity of the object 10 using the data, c) code for determining changes in the shape of the object 10 using the data received from the light detecting elements 11(a), d) code for interpreting the time varying data received from the light detecting elements 11(a), e) code for performing suitable applications such as cross-correlation and fluorescence applications, f) code for generating line scans from the time varying data received from the light detecting elements 11(a), g) code for constructing one or more images from the line scans and/or other data such as rotation or changes in shape of the object 10, h) code for displaying the image, and i) any other suitable code for image processing. The CRM may also include code for performing any of the signal processing or other software-related functions that may be created by those of ordinary skill in the art. The code may be in any suitable programming language including C, C++, Pascal, etc.

The imaging components may also include a display communicatively coupled to the processor. Any suitable display may be used. In one embodiment, the display may be a part of the OFM device 100. The display may provide information such as the image of the object 10 to a user of the OFM device 100. An "imager" can refer to one or more of the image processing components. For example, an imager can be a processor communicatively coupled to a CRM having suitable code.

B. Relaying Components

Some embodiments of the invention include one or more relaying components for communicating light from the light transmissive regions 14($a$) to other components of the OFM device 100. An example of a suitable relaying component is a fiber optic bundle.

Figure 9A:
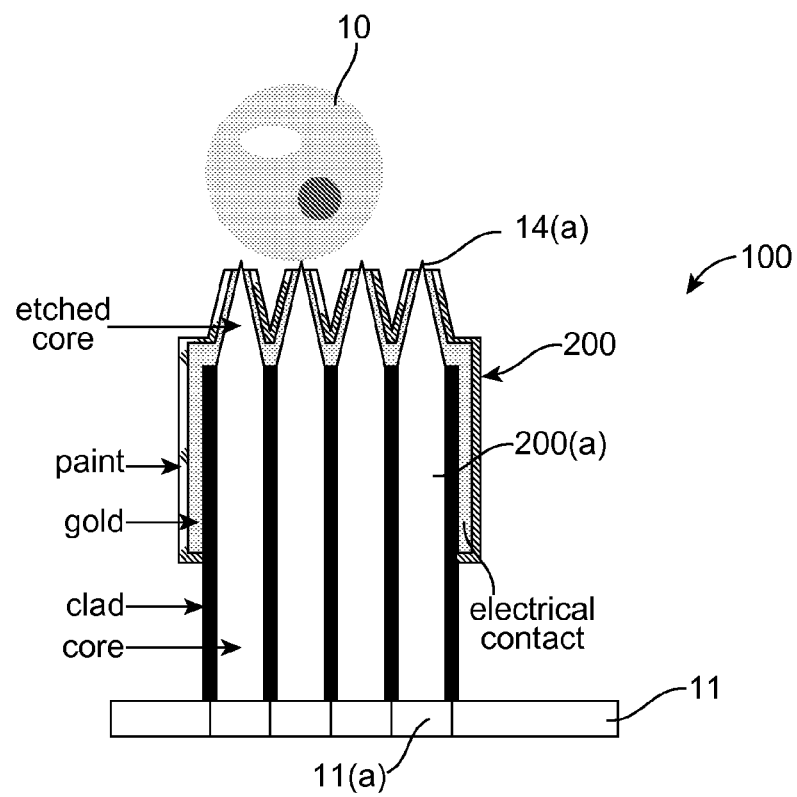
FIG. 9(a) is a schematic drawing of a side view of components of an OFM device including a fiber optic bundle, according to an embodiment of the invention.
Figure 9B:
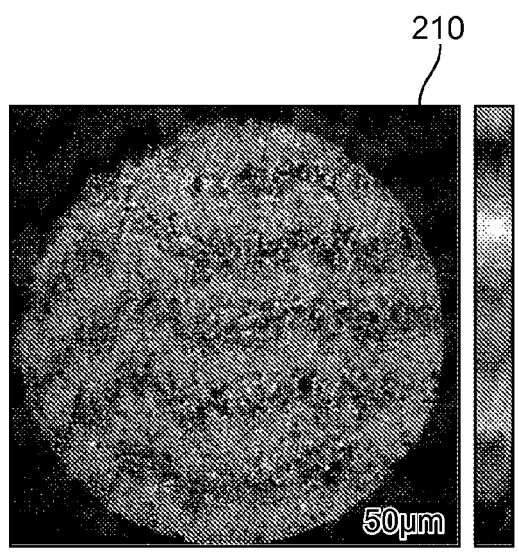
FIG. 9(b) is an image that was generated using the OFM device including the fiber optic bundle of FIG. 9(a), according to an embodiment of the invention.

FIG. 9($a$) is a schematic drawing of a side view of components of an OFM device 100 including a fiber optic bundle 200, according to an embodiment of the invention. The OFM device 100 includes light transmissive regions 14($a$) and a fiber optic bundle 200 having optical fibers 200($a$). Each light transmissive region 14($a$) is associated with a distal end of an optical fiber 200($a$). The proximal ends of the optical fibers 200($a$) are directed to the light detector 11. Each optical fiber 200($a$) may carry the light from a single light transmissive region 14($a$) to a single light detecting element 11($a$) in the light detector 11. This system allows the isolation of the apertures from the detector 11. FIG. 9($b$) is an image generated using an OFM device 100 of FIG. 9($a$).

An example of an OFM device with a fiber bundle 200 can be found in A. Chovin, P. Garrigue, I. Manek-Honninger, N. Sojic, *Fabrication, Characterization, and Far-Field Optical Properties of an Ordered Array of Nanoapertures, Nano Letters* 4, 1965 (October, 2004), which is hereby incorporated by reference in its entirety for all purposes.

III. Systems with Multiple OFM (Optofluidic Microscope) Devices

Multiple OFM devices 100 can be located on a single device in some embodiments. The OFM devices 100 of these embodiments may be arranged in parallel, in series, or in any suitable combination thereof. Multiple OFM devices 100 may provide the capability of automated and parallel imaging of one or more objects 10.

Figure 10:
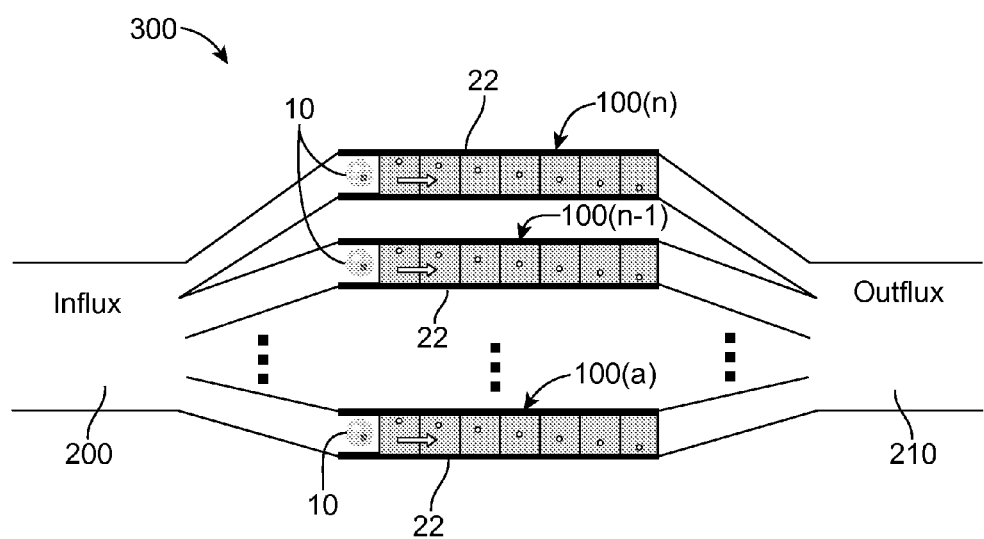
FIG. 10 is a schematic diagram of an OFM system having multiple OFM devices, according to an embodiment of the invention.

FIG. 10 is a schematic diagram of an OFM system 300 having multiple OFM devices 100, according to an embodiment of the invention. In the illustrated example, the OFM devices 100 are arranged in parallel on a single device.

Although the components of each OFM device 100 are arranged according to the first configuration, other configurations can be used. Each OFM device 100 has an aperture layer 14 with light transmissive regions 14($a$) covering light detecting elements 11($a$) in the form of a one-dimensional array extending diagonally across the fluid channel 22. In other embodiments, the light detecting elements 11($a$) may be arranged in other forms. The OFM devices 100 of the OFM system 300 may be located within a single body such as a casing. The overall size dimensions (e.g., width, length, and/or height) of the body may be of any suitable size. In some embodiments, the overall size dimensions (e.g., width, length, and/or height) of the body may be within a range of 20 mm to 2 cm.

The OFM system 300 includes a fluid influx 200 and a fluid outflux 210. The fluid influx 200 branches into N fluid channels 22 that feed into n OFM devices 100($a$)-100($n$). The outlets to the n OFM devices 100($a$)-100($n$) converge to the fluid outflux 210 to the system 300. In operation, a sample with fluid and objects 10 may be introduced at the fluid influx 200. The fluid and objects 10 then flows into the N fluid channels 22 and out through the fluid outflux 210. In OFM system 300, multiple objects 10 can be analyzed and imaged in parallel using the n OFM devices 100.

IV. OFM Applications

Various applications can be performed using OFM devices 100 of embodiments of the invention. Although certain configurations of the components of the OFM devices 100 are shown in the illustrated examples of the applications below, other configurations can be used.

A. Cross-Correlation

Embodiments of the invention can be used to perform cross-correlation and subsequent analyses based on the results from the cross-correlation. Cross correlation can refer to correlating data from two or more sets (e.g., arrays) of light detecting elements 11($a$) or the images generated from the data from the two or more sets of light detecting elements 11($a$). The sets of light detecting elements 11($a$) may be on a single OFM device 100 or may be on multiple OFM devices 100. If the data/images correlate, other analyses may be performed such as the measurement of dimension of the object 10 using the data associated with the correlated data/images.

FIG. 11($a$) is a schematic drawing of components of an OFM device 100, according to an embodiment of the invention. The OFM device 100 has a fluid channel 22 and a light detector 11 with two parallel one-dimensional arrays of light detecting elements 11($a$)(1) and 11($a$)(1). The light detector 11 has been rotated an angle, $\theta$ so that the arrays of light detecting elements 11($a$) are diagonally extending across the fluid channel 22 at an angle, $\theta$ from the x-axis of the fluid channel 22.

The drawing in FIG. 11($a$) includes an expanded view of five light detecting elements 11($a$) of the parallel arrays to show the relative dimensions between the light detecting elements 11($a$). In this example, the pixel size is 1 µm, the distance, L between the light detecting elements 11($a$) along the array axis is 9.9 µm, and the angle between the x-axis and the array axis is $\theta$. The y-directional spacing, $\delta Y$ is 500 nm and the x-directional spacing is $\Delta X$.

Data generated by the two parallel one-dimensional arrays of light detecting elements 11($a$)(1) and 11($a$)(2) can be used to determine the velocity and rotation of the object 10, shape changes in the object 10, and/or flow speed variations during data acquisition. For example, the velocity can be determined from the separation between the two arrays along the x-axis and the time difference between when the object 10 passes over the first light detecting element of the first array light detecting elements 11($a$)(1) and when the object 10 passes over the first light detecting element of the first array light detecting elements 11($a$)(2). The separation between the two arrays along the array axis, $D_1$ is the number of pixels between the first elements multiplied by the pixel size. In this case, the $D_1$=13 pixels×1 µm=13 µm. The separation between the two arrays along the x axis, $D=D_1 \times \cos\theta$.

In addition, two images can be constructed from the two sets of data derived from the two one-dimensional arrays of light detecting elements 11($a$)(1) and 11($a$)(1). The differences between the images can be analyzed to determine shape changes in the object 10, flow speed variations, and/or rotations of the object 10 during data acquisition.

The two images constructed from the two sets of data can also be cross correlated to determine whether the two sets of data are accurate. The cross correlation can be used to screen out inaccurate data/images and/or determine that the data/images are accurate for use in a calculation such as an automatic measurement of the length of the object 10.

Figure 11B:
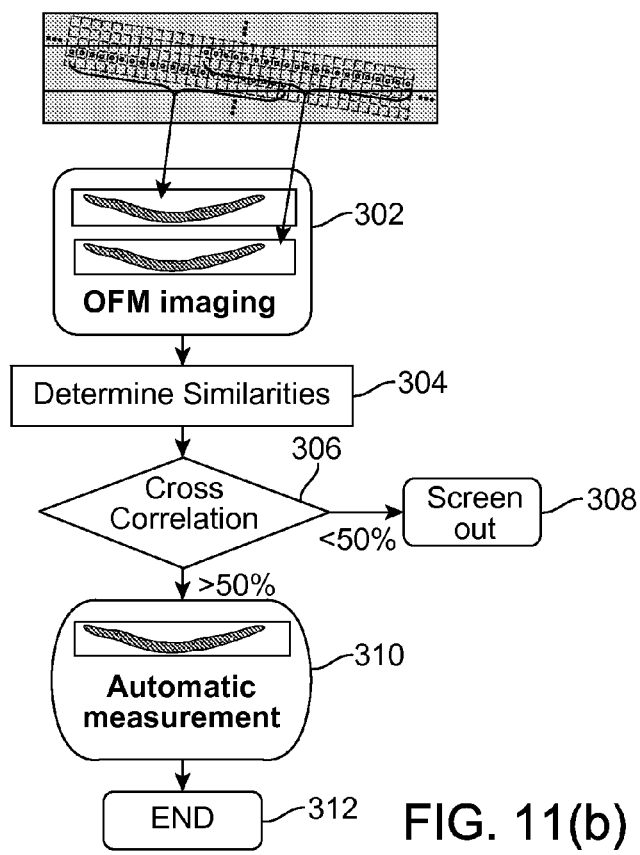
FIG. 11(b) is a flow chart of a method for cross correlating two images of an object generated using an OFM device, according to an embodiment of the invention.

FIG. 11(b) is a flow chart of a method for cross correlating two images of an object 10 generated using an OFM device 100, according to an embodiment of the invention. The method starts with constructing the images from the time varying data derived from the two parallel one-dimensional arrays of light detecting elements 11(a)(1) and 11(a)(1) (step 302). After the images are generated, the similarities between the two constructed images can be determined (step 304). In some cases, the data from each pixel pair of corresponding light detecting elements 11(a) between each of the two parallel one-dimensional arrays is compared. For example, the data from the first light detecting element in the first array may be compared to the data from the first light detecting element in the second array. Based on predefined criteria, the images are cross correlated to determine whether the images are less than or equal to 50% similar or >50% similar (step 306). If the images are less than or equal to 50% similar, then the images are screened out (step 308). If the images are >50% similar, then one or both of the images will be used in an automatic measurement (step 310) and the method ends (step 320).

B. Fluorescence Application

The OFM devices 100 of embodiments of the invention have filters and use fluorescence to image portions of objects 10. Using fluorescence provides the advantage of a more sensitive and quantitative detection of portions of the object 10. Fluorescence is an important functionality of a microscope, especially for biologists and chemists.

Figure 12A:
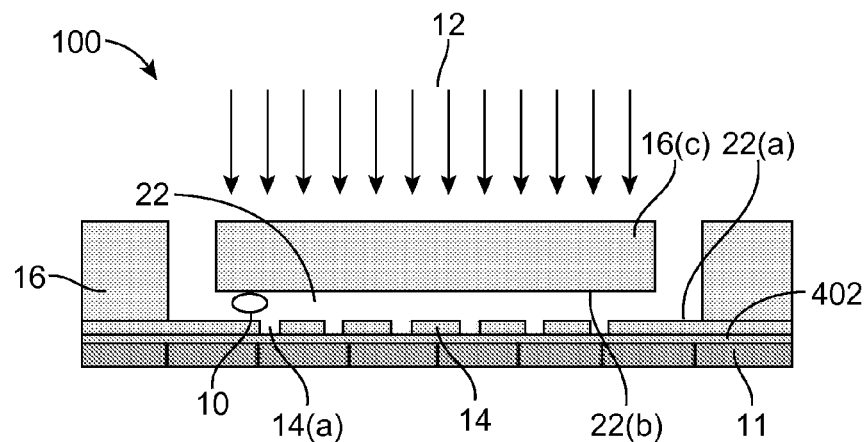
FIG. 12(a) is a schematic drawing of a sectional, side view of components of an OFM device that uses fluorescence to image portions of an object, according to an embodiment of the invention.

FIG. 12(a) is a schematic drawing of a sectional, side view of components of an OFM device 100 that uses fluorescence to image portions of an object 10, according to an embodiment of the invention.

The OFM device 100 includes a body 16 which defines or includes a fluid channel 22. The fluid channel 22 includes a first surface 22(a) and a second surface 22(b) on opposite sides of the fluid channel 22. The first surface 22(a) may correspond to an inner surface at the bottom of the fluid channel 22 and the second surface 22(b) may correspond to the inner surface at the top of the fluid channel 22. The body 16 can be a multi-layer structure or a single, monolithic structure. In the illustrated example, the body 16 is a multi-layer structure having an opaque or semi-opaque aperture layer 14 that is an inner surface layer of the fluid channel 22 having the first surface 22(a). The opaque or semi-opaque aperture layer 14 has light transmissive regions 14(a) in it. The body 16 also includes a transparent layer 16(c).

The illumination source 12 illuminates the transparent layer 16(c) of the body 16. The illumination source 12 may be integrated into the OFM device 100 or may be a separate component (e.g., an external laser). The light from the illumination source 12 may be of any suitable wavelength. In an exemplary embodiment, the light from the illumination source 12 is of certain wavelength(s) (e.g., blue light) that will excite the fluorophores tagged in the object 10. A fluorophore can refer to a component of a molecule which causes the molecule to be fluorescent. The fluorophore can absorb energy of a specific wavelength and re-emit the energy at a different (but equally specific) wavelength.

The OFM device 100 includes a filter 402 on one side of the opaque or semi-opaque aperture layer 14 and a light detector 11 on one side of the filter 402. Filter 402 can refer to any suitable device that allows light of certain wavelengths to pass and reflects light of other wavelengths. Some suitable devices include optical filters (e.g., dichroic filter), dielectric filters, etc. In one exemplary embodiment, the filter 402 is an optical color filter (e.g., a green filter) that allows light of a narrow range of wavelengths associated with a color (e.g., green) and filters out other wavelengths associated with other colors. For example, the illumination source 12 may emit blue light as an excitation light to excite certain fluorophores in portions of the object 10. The fluorophores may re-emit green light in response to being activated by the blue excitation light. The filter 402 can be a green filter that screens out the blue light from the illumination source 12 and allows green light being re-emitted from fluorophores in the object 10 to pass through to the light detector 11. Although the illustrated embodiment includes a single filter 402, other filters can be used in other embodiments. For example, another filter can be placed on a surface of the transparent layer 16(c) that allows the light of wavelengths associated with activating the fluorophores to pass and filters out light of other wavelengths.

The light detector 11 (e.g., photosensor) includes light detecting elements 11(a). The light detecting elements 11(a) may be in any suitable form such as a one-dimensional array, two-dimensional array, multiple one or two-dimensional arrays, or combination thereof. Any suitable light detecting elements can be used.

In one exemplary process, a reagent is mixed with a specimen comprising one or more objects 10. The reagent may be any suitable chemical that can tag (mark) portions (e.g., molecules of a cell nucleus) of the object 10 with fluorophores. The resulting fluid is introduced into the fluid channel 22 of the OFM device 100. As the fluid flows with the object 10 through the fluid channel 22, the illumination source 12 provides an excitation light of wavelength(s) (e.g., blue light) associated with activating the fluorophores. The excitation light passes through the transparent layer 16(c) to the fluid channel 22 to the surface 22(a) and to the surface of the object 10. As the fluid flows through the fluid channel 22, the object 10 passes under the excitation light, which activates the fluorophores in the object 10. The object 10 passes over the light transmissive regions 14(a) which can block light and also light (e.g., green light) can be re-emitted from the fluorophores in portions of the object 10. The excitation light and the light re-emitted from the fluorophores pass through the light transmissive regions 14(a). The filter 402 reflects the excitation light and allows the light re-emitted from the fluorophores to pass through to the light detecting elements 11(a). The light detecting elements 11(a) take time varying data of the intensity of the light. The data is then used to generate images of the object 10 and the portions of the object 10 associated with the fluorophores.

Figure 12B:
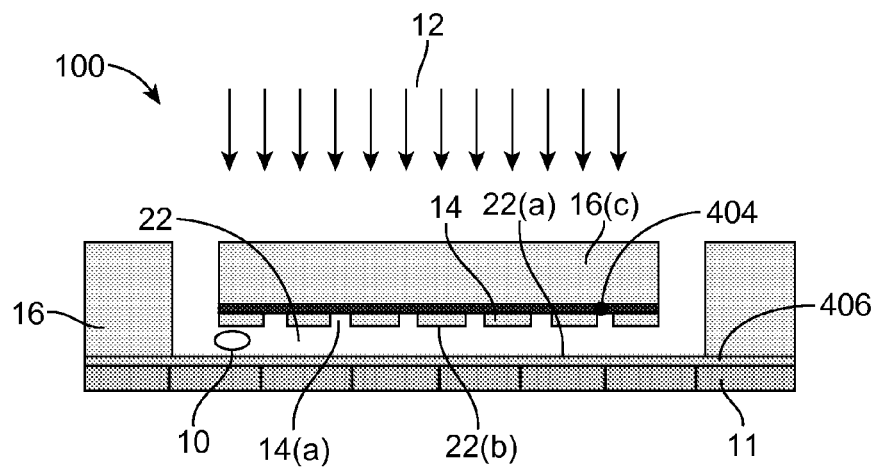
FIG. 12(b) is a schematic drawing of a sectional, side view of an OFM device that uses fluorescence to image portions of an object, according to an embodiment of the invention.

FIG. 12(b) is a schematic drawing of a sectional, side view components of an OFM device 100 that uses fluorescence to image portions of an object 10, according to an embodiment of the invention.

The OFM device 100 includes a body 16 which defines or includes a fluid channel 22. The fluid channel 22 includes a first surface 22(a) and a second surface 22(b) on opposite sides of the fluid channel 22. The first surface 22(a) may correspond to an inner surface at the bottom of the fluid channel 22 and the second surface 22(b) may correspond to the inner surface at the top of the fluid channel 22.

The body 16 can be a multi-layer structure or a single, monolithic structure. In the illustrated example, the body 16 is a multi-layer structure having an opaque or semi-opaque aperture layer 14 that is an inner surface layer of the fluid channel 22 that includes the second surface 22(b). The opaque or semi-opaque aperture layer 14 has light transmissive regions 14(*a*) in it. The body 16 also includes a transparent layer 16(*c*) on the same side of the fluid channel 22 as the opaque or semi-opaque aperture layer 14. A first filter 404 is located between the opaque or semi-opaque aperture layer 14 and the transparent layer 16(*c*). The body 16 also includes a second filter 406 on an inside surface layer of the fluid channel 22 having the first surface 22(*a*). The light detector 11 is located to the outside of the second filter 406. A fluid (not shown) flows with the object 10 through the fluid channel 22.

An illumination source 12 illuminates the transparent layer 16(*c*) of the body 16. The illumination source 12 may be integrated into the OFM device 100 or may be a separate component (e.g., an external laser). The light from the illumination source 12 may be of any suitable wavelength.

First filter 404 and second filter 406 can refer to any suitable devices (e.g., optical filters) that allow light of certain wavelengths to pass and reflect (or absorb) light of other wavelengths. In one exemplary embodiment, the first filter 404 is an optical color filter (e.g., a blue filter) that allows light of a narrow range of wavelengths associated with a color (e.g., blue) that is associated with exciting the fluorophores in the object 10 and filters out other wavelengths. In this example, the illumination source 12 may emit a broad spectrum of light and the filter 404 allows only the light that excites the fluorophores (e.g. blue light) to pass. The fluorophores may re-emit a light of a certain wavelength(s) (e.g., green light) in response. The second filter 406 may be an optical filter (e.g., a green filter) that allows the light being re-emitted from the fluorophores to pass and filters out other wavelengths of light. More of fewer filters can be used in other embodiments. For example, filter 404 can be omitted if the light provided by illumination source is light of a wavelength for exciting the fluorophores in the object 10.

The light detector 11 (e.g., photosensor) includes light detecting elements 11(*a*). The light detecting elements 11(*a*) may be in any suitable form such as a one-dimensional array, two-dimensional array, multiple one or two-dimensional arrays, or combination thereof. Any suitable light detecting elements can be used.

In one exemplary process, a reagent is mixed with a specimen comprising one or more objects 10. The reagent may be any suitable chemical that can tag portions (e.g., molecules of a cell nucleus) of the object 10 with fluorophores. The resulting fluid is introduced into the fluid channel 22 of the OFM device 100. As the fluid flows with the object 10 through the fluid channel 22, the illumination source 12 provides light which passes through the transparent layer 16(*c*). Filter 404 allows the light of wavelength(s) for exciting the fluorophores to pass and reflects light of other wavelengths. For example, filter 404 may be a blue filter that allows a blue excitation light to pass and reflects light of other wavelengths. The excitation light passes through the light transmissive regions 14(*a*) to generate point illumination sources. The excitation light from the point illumination sources illuminates the surface 22(*a*) and the surface of the object 10. As the fluid flows, the object 10 passes under the point illumination sources of excitation light which excites the fluorophores in portions of the object 10 and blocks some light. The excitation light and the light re-emitted from the fluorophores pass through to the surface 22(*a*). Filter 406 reflects the excitation light and allows the light re-emitted from the fluorophores to pass through to the light detecting elements 11(*a*). For example, filter 406 may be a green filter that reflects the blue excitation light and allow the green light re-emitted by the fluorophores to pass. The light detecting elements 11(*a*) take time varying data of the intensity of the light. The data is then used to generate images of the object 10 and the portions of the object 10 associated with the fluorophores.

Some embodiments of the invention include multiple OFM devices 100 having different filters for using fluorescence to image portions of an object 10.

Figure 13A:
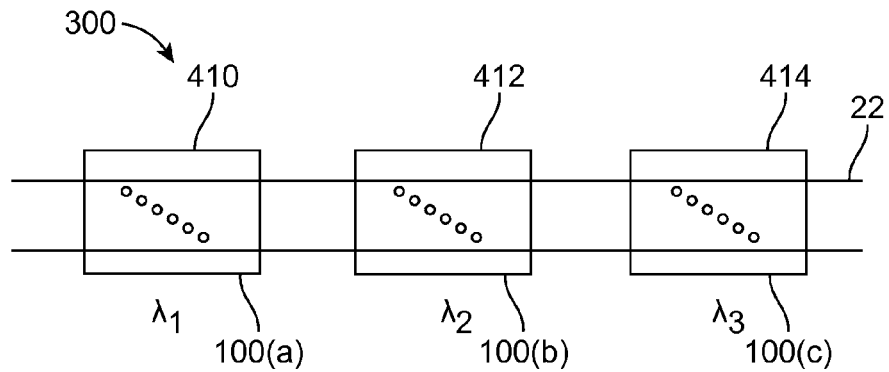
FIG. 13(a) is a schematic drawing of a top view of an OFM system including three OFM devices in series, according to an embodiment of the invention.
Figure 13B:
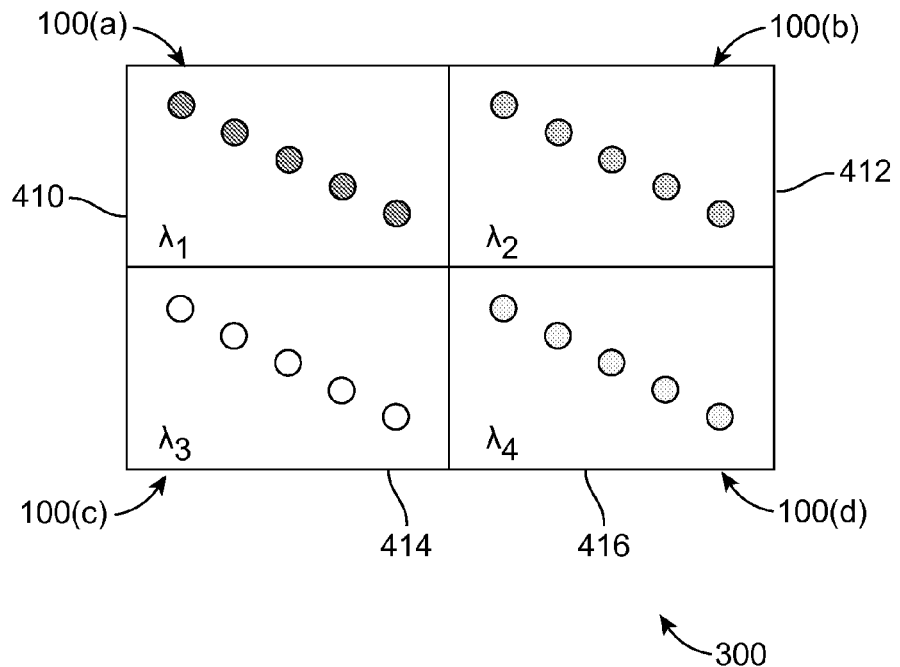
FIG. 13(b) is a schematic drawing of a top view of an OFM system having four OFM devices arranged in a 2×2 two-dimensional array, according to an embodiment of the invention.

FIG. 13(*a*) is a schematic drawing of a top view of an OFM system 300 having three OFM devices 100(*a*), 100(*b*), and 100(*c*) arranged in series, according to an embodiment of the invention. Each of the OFM devices 100(*a*), 100(*b*), and 100(*c*) has a different filter. The OFM device 100(*a*) has a filter 410 which allows light with a wavelength, $\lambda_1$ to pass. The OFM device 100(*b*) has a filter 412 which allows light with a wavelength, $\lambda_2$ to pass. The OFM device 100(*c*) has a filter 414 which allows light with a wavelength, $\lambda_3$ to pass. The OFM devices can be used to generate images from light of wavelengths $\lambda_1$, $\lambda_2$, $\lambda_3$, and $\lambda_4$. In some cases, different structures in objects 10 may re-emit different wavelengths of light. In these cases, each OFM device may have a filter associated with a specific structure. The images generated by each OFM device 100 may identify the different structures associated with the wavelengths.

FIG. 13(*b*) is a schematic drawing of a top view of an OFM system 300 having four OFM devices 100(*a*), 100(*b*), 100(*c*), and 100(*d*) arranged in a 2×2 two-dimensional array, according to an embodiment of the invention. Each of the OFM devices 100(*a*), 100(*b*), 100(*c*), and 100(*d*) has a different filter. The OFM device 100(*a*) has a filter 410 which allows light with a wavelength, $\lambda_1$ to pass. The OFM device 100(*b*) has a filter 412 which allows light with a wavelength, $\lambda_2$ to pass. The OFM device 100(*c*) has a filter 414 which allows light with a wavelength, $\lambda_3$ to pass. The OFM device 100(*d*) has a filter 416 which allows light with a wavelength, $\lambda_4$ to pass.

V. Fluid Flow and Particulate Transport

On the micro and nano scale, fluid flow and particulate transport through the fluid channel 22 can be accomplished using numerous different techniques. The most used techniques include traditional pressure driven flow, electrokinetic transport, discrete droplet translocation via electrowetting, or thermocapillarity techniques. Some other techniques include gravity driven flow, hydrodynamic focusing, dielectrophoresis electrodes, and optical tweezers. Some of these techniques are described below. Although certain configurations of OFM devices 100 are shown in the illustrated examples of the techniques below, other configurations can be used.

A. Gravity Driven Flow

Figure 14:
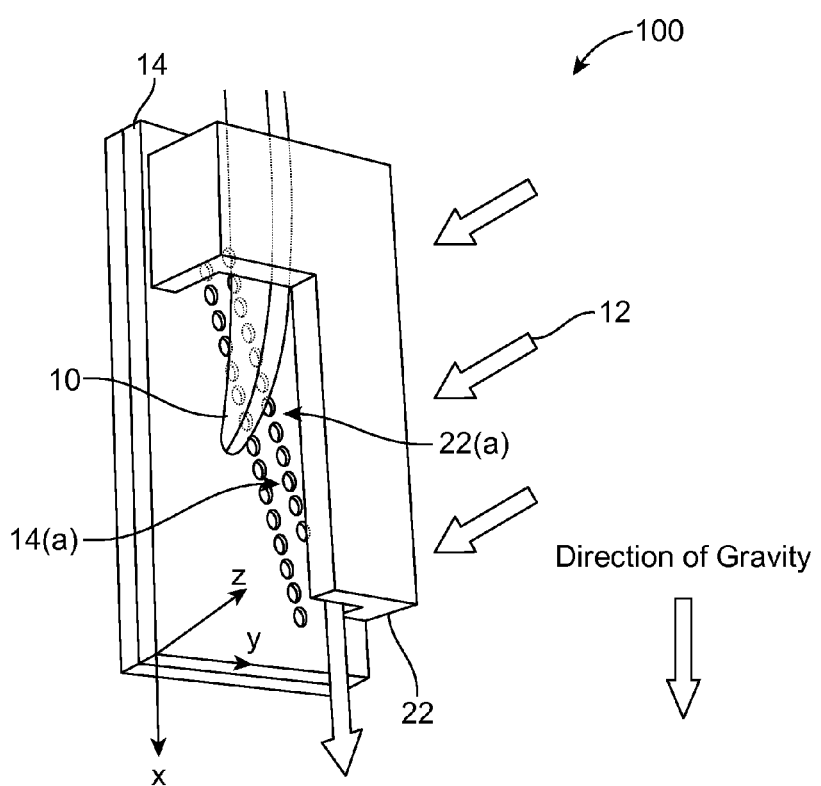
FIG. 14 is a schematic, perspective drawing of components of an OFM device that employs gravity drive flow, according to an embodiment of the invention.

FIG. 14 is a schematic, perspective drawing of components of an OFM device 100 that employs gravity drive flow, according to an embodiment of the invention. The OFM device 100 has a body 16 that forms or includes a fluid channel 22 having a surface 22(*a*), an x-axis, and a y-axis. The body 16 includes an opaque or semi-opaque aperture layer 14 with light transmissive regions 14(*a*).

The OFM device 100 is located so that the x-axis of the fluid channel 22 is substantially in the direction of gravity (downward). In operation, a specimen solution with the object 10 may be introduced into a top portion 450 of the OFM device 100 by any suitable means such as a funnel or a syringe into a port. The specimen solution wets the fluid channel 22 and the objects 10 are continuously pulled into the fluid channel 22 by gravity. One advantage of this embodiment is that using gravity can eliminate the need for bulky pumps.

B. DC Electrokinetics

In many embodiments, generating quality images of objects 10 requires that the objects 10 do not change shape or orientation during the image acquisition process. One technique for maintaining the object 10 at a constant orientation is to use a DC electrokinetic drive (pump). Incorporating a DC electrokinetic drive (pump) into an OFM device 100 may provide a compact means for controlling the flow speed and for ensuring that the objects 10 (e.g., biological samples) maintain a constant orientation during the imaging acquisition process. Using a DC electrokinetic drive may improve the capability of the OFM device 100 to more easily image spherical and ellipsoidal biological entities.

Fluid flow through a fluid channel 22 is generally driven by a pressure difference. The non-slip boundary condition existing on the lateral walls of the fluid channel 22 results in a flow with a laminar velocity profile that is parabolic, which is known as Poiseulle flow. The parabolic velocity profile results in an uneven distribution of drag force on the object 10 moving through the fluid channel 22, which can cause the object 10 to rotate.

Figure 15A:
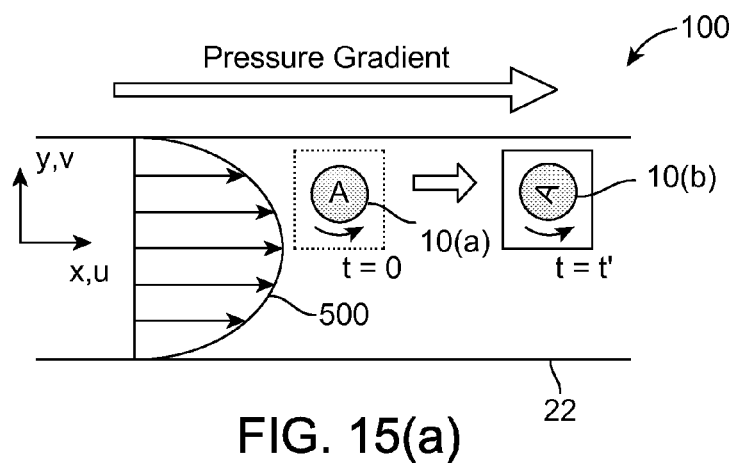
FIG. 15(a) is a schematic drawing of a top view of components of an OFM device having a fluid channel with a parabolic velocity profile, according to an embodiment of the invention.

FIG. 15(a) is a schematic drawing of a top view of components of an OFM device 100 having a fluid channel 22 with a parabolic velocity profile 500, according to an embodiment of the invention. The OFM device 100 has a fluid channel 22 having an x, u-axis and a y, v-axis. The object 10(a) starts moving in the y direction at t=0. The object 10(a) is subjected to the uneven velocity distribution represented by the parabolic velocity profile 500. At t=t', the uneven velocity distribution has caused the object 10(b) to rotate.

DC electrokinetics may provide a simple and direct way to control the motion of objects 10 in an OFM device 100 and suppress the rotation of the object. The DC electrokinetic drive imposes a uniform electric field in the fluid channel 22 using two electrodes placed at opposite ends of the fluid channel 22. This electric field induces a dipole in the object 10 which will align the object 10 along the electric field lines due to the electro-orientation effect. At the same time, the object 10 which typically carries a net negative charge will be subjected to an electrophoretic force which can translate the object 10 through the fluid channel 22. The velocity dependent viscous Stokes drag will eventually balance with this force and result in a constant rotation-free translational motion of the object 10 through the fluid channel 22.

The lateral walls of the fluid channel 22 are likely to be surface charged. There is an accumulation of counterions building up adjacent to the channel walls, forming the electric double layer (EDL). The application of the external electric field also causes the translation of the electric double layer (EDL) at the surface charged channel walls. This phenomenon is known as electroosmosis. Under the thin EDL assumption, the electroosmotic plug-like constant velocity profile will exert a symmetrical shear stress distribution and constant net force on the object 10. In steady-state situations, the resultant movement is also non-rotational.

Figure 15B:
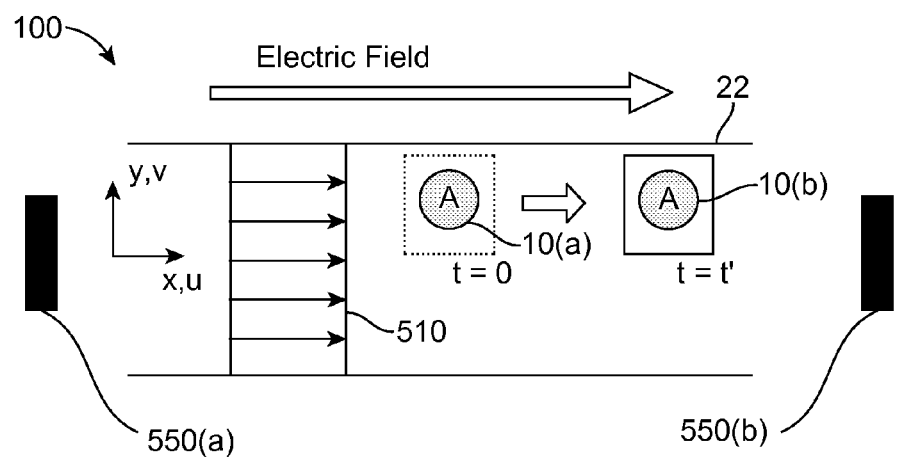
FIG. 15(b) is a schematic drawing of a top view of components of an OFM device having a fluid channel with the constant velocity profile, according to an embodiment of the invention.

FIG. 15(b) is a schematic drawing of a top view of components of an OFM device 100 having a fluid channel with the constant velocity profile 510, according to an embodiment of the invention. The OFM device 100 has a fluid channel 22 having an x, u-axis and a y, v-axis. The OFM device 100 also has a first electrode 550(a) and a second electrode 550(b) at opposite ends of the fluid channel 22. The first electrode 550(a) and a second electrode 550(b) imposes a uniform electric field 510 in the fluid channel 22 that causes a constant net force on the object 10 creating the constant velocity profile 510. As the object 10(a) starts at t=0 to move through the fluid channel 22, the object 10(a) is under the constant velocity profile 510 which causes pure translation without rotation. At t=t', the object 10(b) has translated to a new position under the constant velocity profile 510 without rotation.

C. Hydrodynamic Focusing

Hydrodynamic focusing may improve throughput rates as well as provide control over the motion of objects 10 in the fluid channel 22 during image acquisition.

Figure 16:
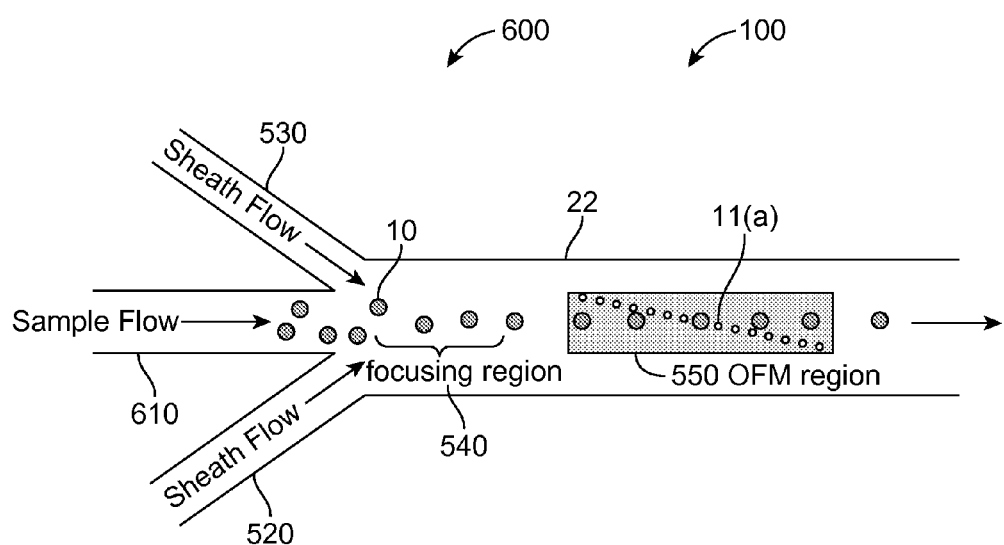
FIG. 16 is a schematic drawing of a top view of components of an OFM device with a hydrodynamic focusing unit, according to an embodiment of the invention.

FIG. 16 is a schematic drawing of a top view of components of an OFM device 100 with a hydrodynamic focusing unit 600, according to an embodiment of the invention. The hydrodynamic focusing unit 600 includes an injection unit 610 that introduces the specimen suspension with objects 10 into the hydrodynamic focusing unit 600. The hydrodynamic focusing unit 600 also includes a first focusing unit 520 and second focusing unit 530 that create sheath streams to move the objects 10 into the center (to the centerline) or another appropriate location of the fluid channel 22. The objects 10 move through a focusing region 540 where the objects 10 can be stabilized to translate without rotation into the OFM region 550. In the OFM region 550, the objects 10 will pass over the light detecting elements 11(a) in the fluid channel 22. In other embodiments, an aperture layer 14 with light transmissive regions 14(a) may cover the light detecting elements 11(a).

The throughput rate of the OFM device 100 with the hydrodynamic focusing unit 600 is determined by the flow rate of the first focusing unit 520 and second focusing unit 530, the differential pressure before the first focusing unit 520 and second focusing unit 530 and the injection unit 510, and the viscosity of the specimen suspension. In some embodiments, the throughput rate may range from 500-1000 objects per minute.

D. Dielectrophoresis (DEP) Flow to Keep Objects Proximal to Surface

In some embodiments, the resolution of the images being imaged by the OFM device 100 can be improved and potentially maximized by ensuring that the object 10 translates in a plane just above the surface 22(a) above the aperture layer 14 having light transmissive regions 14(a).

In one embodiment, the object 10 may be physically confined to this plane above the surface 22(a) due to the geometry of the fluid channel 22. To confine the object 10 to the plane requires that the size of the fluid channel 22 be on the order of the object 10 being imaged, which for smaller objects (<0.5 micron) may mean a channel size on the order of hundreds of nanometers. In addition, physical confinement using the geometry of the fluid channel 22 may not be effective for specimens with objects 10 of very different sizes.

Dielectrophoresis is a phenomenon in which a force is exerted on a object when it is subjected to a non-uniform electric field. The dielectrophoretic force can cause the object 10 to move either up or down the non-uniform electric field. This force does not require that the object 10 be charged. However, the strength of the force will depend on the electrical charge of the object 10. The strength of the force will also depend on the object's shape and size, as well as on the frequency of the electric field. Using electric fields of particular frequencies, objects 10 can be selectively manipulated based on their charge and geometry.

Figure 17:
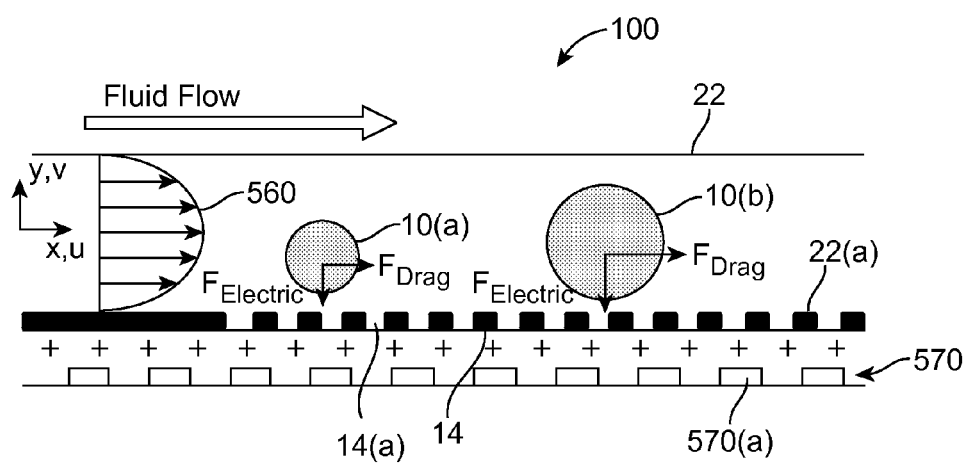
FIG. 17 is a schematic drawing of a side view of components of an OFM device subjected to a non-uniform electric field, according to an embodiment of the invention.

FIG. 17 is a schematic drawing of a side view of components of an OFM device 100 subjected to a non-uniform electric field, according to an embodiment of the invention. The OFM device 100 has a fluid channel 22 having an x, u-axis and a y, v-axis. The fluid channel 22 is subjected to an uneven velocity distribution represented by the parabolic velocity profile 560. The fluid channel 22 includes aperture layer 14 having light transmissive regions 14(a). The fluid channel 22 also has an electrode layer 570 with electrodes 570(a) that create a non-uniform electric field. An object 10(a) and 10(b) are in the fluid channel 22. The object 10(a) is of a larger size than the object 10(b). Since the sizes are different, the forces from the non-uniform electric field and/or from the uneven velocity distribution are different. The $F_{electric}$ and $F_{drag}$ forces on the smaller object 10(a) are smaller in comparison to the $F_{electric}$ and $F_{drag}$ forces on the larger 10(b).

Many objects 10 such as biological cells have electric charges, either positive or negative. By imposing an opposite charge on the surface 22(a) of the body 16 having the light transmissive regions 14(a), the objects 10 can be attracted to the surface 22(a) and may be trapped to translate just above the surface 22(a). A charge can be imposed using any suitable manner such as by coating a thin layer of charged polymer on the surface 22(a) or by using an electrode.

E. Optical Tweezers

Optical tweezers can provide a high-precision method for manipulation of the object 10 including controlling the translation and rotation of the object 10. An exemplary OFM device 100 using an optical tweezer can be found in X. Heng, E. Hsiao, D. Psaltis, C. Yang, *An optical tweezer actuated, nanoaperture-grid based Optofluidic Microscope implementation method*, Optics Express 15, 16367 (2007), which is hereby incorporated by reference in its entirety for all purposes.

Figure 18:
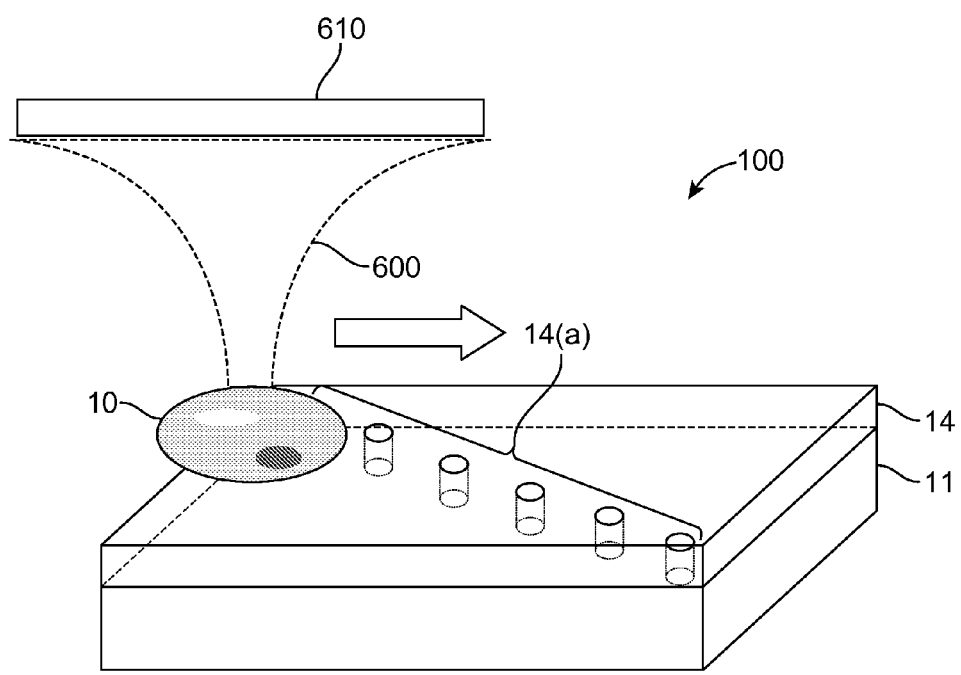
FIG. 18 is a schematic drawing of a perspective view of components of an OFM device employing an optical tweezer to control the movement of the object, according to an embodiment of the invention.

FIG. 18 is a schematic, perspective drawing of components of an OFM device 100 employing an optical tweezer 600 to control the movement of an object 10, according to an embodiment of the invention. The OFM device 100 includes an opaque or semi-opaque aperture layer 14 that has light transmissive regions 14(a). The OFM device 100 also includes a light detector 11 to the outside of the opaque or semi-opaque aperture layer 14. The optical tweezer 60 uses a laser 610 to generate a focused laser beam which attracts the object 10 as outlined in X. Heng, E. Hsiao, D. Psaltis, C. Yang, *An optical tweezer actuated, nanoaperture-grid based Optofluidic Microscope implementation method*, Optics Express 15, 16367 (2007). By moving the focused laser beam, the object 10 can be moved across the light transmissive regions 14(a). While the object 10 is being translated by the optical tweezer 600, the object 10 does not rotate. The optical tweezer 60 provides the ability to control the translational and rotational movement of the object 10. By controlling the movement of the focused laser beam, the speed of the object 10 can also be controlled.

It should be understood that the present invention as described above can be implemented in the form of control logic using computer software in a modular or integrated manner. Other ways and/or methods to implement the present invention using hardware and a combination of hardware and software may also be used.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. An optofluidic microscope device comprising:
    a body defining a fluid channel having a longitudinal axis, the body including a surface layer proximal to the fluid channel; and
    a one-dimensional array of light detecting elements located within the surface layer, wherein the light detecting elements are configured to receive light passing through the fluid channel and generate time-varying data associated with the received light as an object passes through the fluid channel, wherein the one-dimensional array of light detecting elements extends substantially from a first lateral side to a second lateral side of the fluid channel.

2. The optofluidic microscope device of claim 1, wherein a spacing between the light detecting elements in a first direction orthogonal to the longitudinal axis of the flow channel, is substantially less than a size of the light detecting elements.

3. The optofluidic microscope device of claim 1, wherein the body further comprises a transparent layer between the fluid channel and the surface layer.

4. The optofluidic microscope device of claim 1, further comprising a processor in electronic communication with the one-dimensional array of light detecting elements and configured to generate line scans based on the data, and to assemble the line scans to generate an image of an object moving through the fluid channel.

5. A method comprising:
    causing an object to move through a fluid channel;
    providing light to the fluid channel using an illumination source while the object is moving through the fluid channel;
    receiving light from the illumination source passing through the fluid channel with an array of light detecting elements located in a surface layer of a body of the optofluidic microscope device, wherein the surface layer is proximal to the fluid channel, wherein the one-dimensional array of light detecting elements extends substantially from a first lateral side to a second lateral side of the fluid channel;
    generating data associated with the received light by the array of light detecting elements;
    generating line scans using a processor based on the data generated by the array of light detecting elements; and
    assembling the line scans using the processor to generate an image of the object.

6. An optofluidic microscope device comprising:
    a body defining a fluid channel, the body including an aperture surface layer proximal to the fluid channel and on a first side of the fluid channel, and an additional layer on a second side of the fluid channel opposing the first side;
    an illumination source configured to provide illumination into the fluid channel through light transmissive regions in the aperture surface layer; and a one-dimensional array of light detecting elements located in the additional layer, wherein the light detecting elements are configured to receive light from the fluid channel and generate time varying data associated with the received light.

7. An optofluidic microscope device comprising:
a body defining a fluid channel, the body including a surface layer proximal to the fluid channel;
a plurality of slits in the surface layer, wherein the slits have different orientations with respect to a longitudinal axis of the fluid channel; and
light detecting elements in the body, and configured to receive light through the slits and generate time varying data associated with the received light.

8. An optofluidic microscope device system, comprising:
an influx for receiving a sample; a body having a surface layer;
a plurality of optofluidic microscope devices, each optofluidic microscope device comprising:
a fluid channel defined by the body, and adapted to receive a portion of the sample from the influx, wherein the surface layer of the body is proximal to the fluid channel;
a one-dimensional array of light detecting elements located within the surface layer, wherein the light detecting elements are configured to receive light passing through the fluid channel and generate time-varying data associated with the received light as the sample passes through the fluid channel, wherein the one-dimensional array of light detecting elements extends substantially from a first lateral side to a second lateral side of the fluid channel.

9. The optofluidic microscope device of claim 8, wherein the body has a size of less than 2 cm.

* * * * *